United States Patent [19]

Kobori et al.

[11] Patent Number: 6,066,672

[45] Date of Patent: May 23, 2000

[54] AMINO COMPOUNDS AND ANGIOTENSIN IV RECEPTOR AGONISTS

[75] Inventors: Takeo Kobori, Atsugi; Kenichi Goda, Sagamihara; Kikuo Sugimoto, Kanagawa; Tomomi Ota; Kazuyuki Tomisawa, both of Tokyo, all of Japan

[73] Assignees: Taisho Pharmaceutical Co., Ltd., Tokyo; Sagami Chemical Research Center, Sagamihara, both of Japan

[21] Appl. No.: 09/101,449

[22] PCT Filed: Aug. 5, 1997

[86] PCT No.: PCT/JP97/02716

§ 371 Date: Jul. 16, 1998

§ 102(e) Date: Jul. 16, 1998

[87] PCT Pub. No.: WO98/05624

PCT Pub. Date: Feb. 12, 1998

[30] Foreign Application Priority Data

Aug. 6, 1996 [JP] Japan ................................ 8-207010

[51] Int. Cl.⁷ ...................... A61K 31/165; C07C 233/05
[52] U.S. Cl. .................... 514/620; 514/307; 514/311; 514/357; 514/538; 514/626; 514/649; 546/139; 546/176; 546/329; 560/39; 564/165; 564/168; 564/198; 564/337
[58] Field of Search ..................... 564/165, 198, 564/168, 337; 514/620, 626, 307, 311, 357, 538, 649; 546/139, 176, 329; 560/39

[56] References Cited

U.S. PATENT DOCUMENTS 5,439,919 8/1995 Miyachi et al. ..................... 514/316

OTHER PUBLICATIONS

Krebs, et al., Characterization of the binding properties and physiological action of divalinal–angiotensin IV, a putative AT4 receptor Antagonist', Regul. Pept., 67 (28) (1996) p. 123130.

Sardinia, et al., "AT4 receptor binding relationship; N–terminal–modified angiontensin IV analogues", Peptides (Tarrytown, N.Y.)15(8) (1994), pp. 1399–1406.

Bernier, et al., "Characterization of a binding site for angiotensin IV on bovine aortic endothelial cells", Eur. J. Pharmacol., Mol. Pharmacol., Sect., 291(2) (1995) pp. 191–200.

Bernier, et al., "A specific binding site recognizing a fragment of angiotensin II in bovine adrenal cortex membranes"., Eur. J. Pharmacol., 271(1) (1994) pp. 55–63.

Hall, et al., "Identification and characterization of a novel angiotensin binding site in cultured vascular smooth muscle cells that is specific for the hexapeptide (3–8) fragment of angiotensin II angiotensin IV", Regul. Pept., 44(2) (1993) pp. 225–232.

Swanson, et al., "Discovewry of a distinct binding site for angiotensin II (3–8), a putative angiotensin IV receptor", Regul. Pept., 40(3) (1992) pp. 409–419.

WO, 94/00492, A1, Jan. 6, 1994.

Haberl, et al., "Angiotensin Degradation Products Mediate Endothelium–Dependent Dilation of Rabbit Brain Arterioles", Circ. Res., 68(6) (1991) pp. 1621–1627.

Baker, et al., "Angiontensin II stimulation of protein synthesis and cell growth in chick heart cells", Am. J. Physical. 259 (1990) H610–H618.

Miller–Wing, et al., "Central angiotensin IV Binding sites: Distribution and specificity in Guinea Pig Brain", J. Phamracol. Exp. Thr. 266(3) (1993) pp. 1718–1726.

*Primary Examiner*—Shailendra Kumar
*Attorney, Agent, or Firm*—Armstrong, Westerman, Hattori, McLeland & Naughton

[57] ABSTRACT

The present invention provides an amino compound represented by Formula:

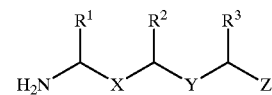

wherein X is $CH_2NH$ or $CONH$, Y is $CH_2NH$ or $CONH$ with the proviso that X and Y are not $CONH$ at the same time; Z is $CH=C(R^4)R^5$, $CH_2CH(R^4)R^5$ or an alkoxycarbonyl group, $R^1$ is a hydrogen atom; a lower alkyl group, a cycloalkyl group, a cycloalkyl-substituted alkyl group, an aralkyl group or an aryl group, each group of which is substituted or unsubstituted, $R^2$ and $R^3$ are each independently a lower alkyl group or an aralkyl group, each group of which is substituted or unsubstituted, and $R^4$ and $R^5$ are each independently a hydrogen atom; an alkyl group, an aralkyl group, an aryl group or a heteroaryl group, each group of which is substituted or unsubstituted, or a pharmaceutically acceptable salt thereof; a medicine comprising the amino compound of Formula (1) or a pharmaceutically acceptable salt; and an angiotensin IV receptor agonist containing the same as an effective component, which are useful, in particular, as a therapeutical drug (antagonist or agonist) for various diseases in which angiotensin IV participates, for example, acceleration of renal blood flow, cerebral vasodilation, inhibition of cell proliferation and hypermnesia.

12 Claims, No Drawings

AMINO COMPOUNDS AND ANGIOTENSIN IV RECEPTOR AGONISTS

This application is a 371 of PCT/JP97/02716, filed Aug. 5, 1997

TECHNICAL FIELD

The present invention relates to amino compounds useful as medicines, and in particular it relates to amino compounds useful as therapeutical drugs for various diseases in which angiotensin IV participates.

BACKGROUND ART

In the renin-angiotensin system, peptides relating to coronary vessels and electrolyte homeostasis are produced by the enzymatic peptide-degradation cascade. In the cascade, angiotensinogen is first converted by renin into physiologically inert angiotensin I, angiotensin II, angiotensin III and finally into angiotensin IV which is a hexapeptide, successively. Angiotensin IV receptor is known to be distributed at high concentration in various organs such as brain (in particular, hippocampus), adrenal gland, heart, kidney, smooth muscle cells and endothelial cells. It is also reported that angiotensin IV relates to various physiological functions such as acceleration of renal blood flow (Swanson et al., Regulatory Peptides, 1992, 40, 409), cerebral vasodilation (Haberl et al., Circ. Res., 1991, 68, 1621), inhibition of cell proliferation (Barker and Aceto, Am. J. Physio., 1990, 259, H610) and hypermnesia (Miller-Wing, et al., J. Pharmacol. Exp. Thr., 1993, 266, 1718).

On the other hand, some peptide compounds are reported to act on angiotensin IV receptor agonistically (Sardinia, et al., Peptides, 1993, 14, 949; ibid., 1994, 8, 1399). However, these peptides should be composed of at least 5 amino acids to express high activities and have some problems in safety and the like. The amino compounds of the present invention have not been known.

DISCLOSURE OF THE INVENTION

As a result of extensive researches in order to provide amino compounds which agonistically act on the angiotensin IV receptor at low concentration, the present inventors have found that specific amino compounds agonistically act on the angiotensin IV receptor strongly, and thereby the present invention has been accomplished.

The present invention relates to an amino compound represented by the following Formula (1):

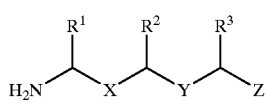

(1)

wherein X is $CH_2NH$ or $CONH$, Y is $CH_2NH$ or $CONH$ with the proviso that X and Y are not $CONH$ at the same time; Z is; $CH=C(R^4)R^5$, $CH_2CH(R^4)R^5$ or an alkoxycarbonyl group, $R^1$ is a hydrogen atom; a lower alkyl group, a cycloalkyl group, a cycloalkyl-substituted alkyl group, an aralkyl group or an aryl group, each group of which is substituted or unsubstituted, $R^2$ and $R^3$ are each independently a lower alkyl group or an aralkyl group, each group of which is substituted or unsubstituted, and $R^4$ and $R^5$ are each independently a hydrogen atom; an alkyl group, an aralkyl group, an aryl group or a heteroaryl group, each group of which is substituted or unsubstituted; or a pharmaceutically acceptable salt thereof. Additionally, the present invention provides a medicine or angiotensin IV receptor agonist, comprising the amino compound of Formula (1) or the pharmaceutically acceptable salt thereof as an effective component.

In the present specification, the definitions used in the general formulae have the following means, unless otherwise noted.

The alkoxycarbonyl group is preferably a $C_2$–$C_{10}$ alkoxycarbonyl group, specific examples of which are a methoxycarbonyl group, an ethoxycarbonyl group, a propoxycarbonyl group, an allyloxycarbonyl group and a benzyloxycarbonyl group.

The lower alkyl group refers to a straight or branched $C_1$–$C_6$ alkyl group, and specific examples of the alkyl group which is unsubstituted are a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group and a 1-ethyl-2-methylpropyl group.

The alkyl group is preferably a straight or branched $C_1$–$C_{12}$ alkyl group, specific examples of the alkyl group which is unsubstituted include the above-mentioned lower alkyl group, a heptyl group, an octyl group, a nonyl group, a decyl group, a dodecyl group, an iso-form, a sec-form and a tert-form thereof.

The alkenyl group is preferably a straight or branched $C_2$–$C_6$ alkenyl group, specific examples of the alkenyl group which is unsubstituted are a vinyl group, an allyl group, a 1-propenyl group, a 1-butenyl group, a 2-butenyl group, a 3-butenyl group, a 2-methyl-1-propenyl group, a 2-methyl-2-propenyl group, a 1-pentenyl group, a 2-pentenyl group, a 3-pentenyl group, a 4-pentenyl group, a 3-methyl-1-butenyl group, a 3-methyl-2-butenyl group, a 3-methyl-3-butenyl group, a 2-methyl-1-butenyl group, a 2-methyl-2-butenyl group, a 2-methyl-3-butenyl group, a 2-ethyl-2-propenyl group, a 1-methyl-1-butenyl group, a 1-methyl-2-butenyl group, a 1-methyl-3-butenyl group, a 1-hexenyl group, a 2-hexenyl group, a 3-hexenyl group, a 4-hexenyl group, a 5-hexenyl group, a 4-methyl-3-pentenyl group and a 2,3-dimethyl-2-butenyl group.

The cycloalkyl group is preferably $C_3$–$C_8$ cycloalkyl group, and examples of the cycloakyl group which is unsubstituted are a cyclopropyl group, a cyclobutyl group, a cyclopentyl group, a cyclohexyl group, a cycloheptyl group and a cyclooctyl group.

The cycloalkyl-substituted alkyl group is preferably a cycloalkyl-substituted alkyl group having 4 to 10 carbon atoms, and specific examples of the cycloalkyl-substituted alkyl group which is unsubstituted are a cyclopropylmethyl group, a cyclopropylbutyl group, a cyclobutylpropyl group, a cyclopentylethyl group, a cyclohexylmethyl group, a cycloheptylmethyl group and a cyclooctylethyl group.

The aralkyl group refers to an alkyl group which is substituted with an aryl group including a heteroaryl group, and specific examples of the aralkyl group which is unsubstituted are a benzyl group, a phenethyl group, a phenyl-propyl group, a phenylbutyl group, a naphthylmethyl group, a naphthylethyl group, a naphthylpropyl group, a naphthylbutyl group, a diphenylmethyl group, a diphenylpropyl group, a diphenylbutyl group, a biphenylmethyl group, a biphenylethyl group, a biphenylpropyl group, a biphenylbutyl group, a pyrrolylmethyl group, a furylmethyl group, a thienylethyl group, an imidazolylpropyl group, a pyrazolylmethyl group, an oxazolylethyl group, a thiazolylbutyl group, a triazolylpentyl group, a thiadiazolylhexyl group, a pyridylmethyl group, a pyrazinylpropyl group, a pyrimidylheptyl group, a pyridazylethyl group, an indolylbutyl group, a benzofurylmethyl group, a benzothienylethyl group, a benzimidazolyloctyl group, a benzoxazolylethyl group, a benzothiazolylmethyl group, a benzotriazolylbutyl group, a quinolylmethyl group, an isoquinolylethyl group, a phthalazinylpropyl group, a pyrrolidinylmethyl group, a piperidinylethyl group and a piperazinylbutyl group.

The aryl group refers to an aryl group which includes a heteroaryl group, specific examples of the aryl group which is unsubstituted are a phenyl group, a naphthyl group, a biphenyl group, an anthranil group, a pyrrolyl group, a furyl group, a thienyl group, an imidazolyl group, a pyrazolyl group, an oxazolyl group, a thiazolyl group, a triazolyl group, a thiadiazolyl group, a pyridyl group, a pyrazinyl group, a pyrimidyl group, a pyridazyl group, an indolyl group, a benzofuryl group, a benzothienyl group, a benzimidazolyl group, a benzoxazolyl group a benzothiazolyl group, a benzotriazolyl group, a quinolyl group, an isoquinolyl group, a phthalazinyl group, a pyrrolidinyl group, a piperidinyl group and a piperazinyl group.

Examples of the substituent of the above-mentioned groups are a halogen atom (e.g. a chlorine atom, a bromine atom, iodine atom or a fluorine atom), a nitro group, a hydroxyl group, a formyl group, a carboxyl group, a cyano group, a carbamoyl group, an alkyl group (e.g. a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group or a 1-ethyl-2-methylpropyl group), an aryl group (e.g. a phenyl group, a p-tolyl group, an m-fluorophenyl group, an o-chlorophenylnaphthyl group, a biphenyl group, an anthranil group, a pyrrolyl group, a furyl group, a thienyl group, an imidazolyl group, a pyrazolyl group, an oxazolyl group, a thiazolyl group, a triazolyl group, a thiadiazolyl group, a pyridyl group, a pyrazinyl group, a pyrimidyl group, a pyridazyl group, an indolyl group, a benzofuryl group, a benzothienyl group, a benzimidazolyl group, a benzoxazolyl group, a benzothiazolyl group, a benzotriazolyl group, a quinolyl group, an isoquinolyl group, a phthalazinyl group, a pyrrolidinyl group, a piperidinyl group or a piperazinyl group), a polyfluoroalkyl group (e.g. a trifluoromethyl group, a pentafluoroethyl group or a 3,3,3-trifluoropropyl group), an alkenyl group (e.g. a vinyl group or a propenyl group), an alkynyl group (e.g. an ethenyl group or a propargyl group), an alkoxycarbonyl group (e.g. a methoxycarbonyl group, an ethoxycarbonyl group, a propoxycarbonyl group or a benzyloxycarbonyl group), an acyl group (e.g. an acetyl group, a propionyl group, a butyryl group, an isobutyryl group, a valeryl group, an isovaleryl group, a pivaloyl group, a benzoyl group, a 4-methylbenzoyl group, a 3-methylbenzoyl group, a 2-methylbenzoyl group, a naphthoyl group, a nicotinoyl group or an isonicotinoyl group), an amino group (e.g. an amino group, a methylamino group, an ethylamino group, a propylamino group, an isopropylamino group, a butylamino group, an isobutylamino group, a sec-butylamino group, a tert-butylamino group, a pentylamino group, an isopentylamino group, a hexylamino group, a dimethylamino group, a diethylamino group, a dipropylamino group, a diisopropylamino group, a dibutylamino group, an ethylmethylamino group, a methylpropylamino group, an ethylpropylamino group), an oxy group (e.g. a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a 1-methylbutoxy group, a 2-methylbutoxy group, a 1,2-dimethylpropoxy group, a hexyloxy group, a benzyloxy group, a p-methybenzyloxy group, an o-fluorobenzyloxy group, a phenethyloxy group, a biphenylmethoxy group, a pyridylmethoxy group, a naphthylmethoxy group or a phenoxy group), a thio group (e.g. a thiol group, a methylthio group, an ethylthio group, a propylthio group, an isopropylthio group, a butylthio group, an isobutylthio group, a sec-butylthio group, a tert-butylthio group, a pentylthio group, a hexylthio group, a benzylthio group, a phenethylthio group, a biphenylmethylthio group, a pyridylmethylthio group, a naphthylmethylthio group or a phenylthio group), and a sulfonyl group (e.g. a methanesulfonyl group, a benzylsulfonyl group or a benzenesulfonyl group).

Among the amino compounds of the above Formula (1) of the present invention, in view of high activity, preferable are compounds wherein X is $CH_2NH$, and among the compounds, in particular, preferable are the compounds wherein Y is CONH.

Among the amino compounds of the above Formula (1) of the present invention, in view of high activity, preferable are compounds wherein $R^2$ is a 4-hydroxybenzyl group, that is, amino compounds represented by the following Formula (2):

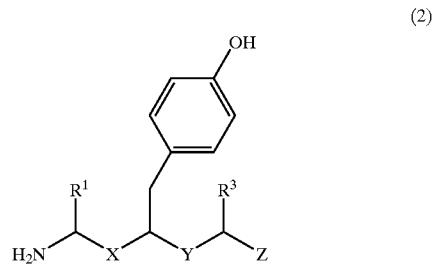

(2)

wherein X, Y, Z, $R^1$ and $R^3$ are as defined above.

Among the amino compounds of the above Formula (2) of the present invention, in view of high activity, preferable are compounds wherein X is $CH_2NH$, $R^1$ and $R^3$ are each a lower alkyl group or an aralkyl group, each group of which is substituted or unsubstituted, and Z is $CH=C(R^4)R^5$ or $CH_2CH(R^4)R^5$, that is, amino compounds represented by the following Formula (3):

(3)

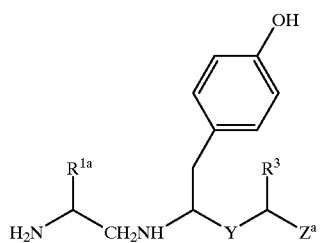

wherein Y and $R^3$ are as defined above, $Z^a$ is $CH=C(R^4)R^5$ or $CH_2CH(R^4)R^5$, $R^{1a}$ is a lower alkyl group or an aralkyl group, each group of which is substituted or unsubstituted.

Among the amino compounds of the above Formula (3) of the present invention, in view of high activity, preferable are compounds wherein $R^3$ is a lower alkyl group which is substituted or unsubstituted, and $Z^a$ is $CH=C(R^4)R^5$, that is, amino compounds represented by the following Formula (4):

(4)

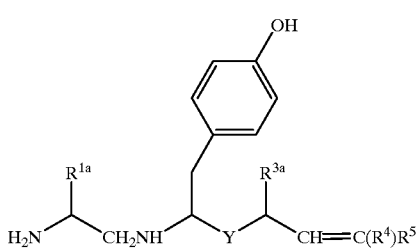

wherein Y, $R^{1a}$, $R^4$ and $R^5$ are as defined above, and $R^{3a}$ is a lower alkyl group which is substituted or unsubstituted.

In addition, among the amino compounds of the above Formula (4) of the present invention, in view of high activity, preferable are compounds wherein $R^{1a}$ is a group selected from the group consisting of a propyl group, an isopropyl group, a butyl group, an isobutyl group, a sec-butyl group and a 2-methylthioethyl group.

The amino compounds of the above Formula (1) of the present invention can form pharmaceutically acceptable salts thereof. Specific examples of these salts, when acidic groups are contained therein, are metal salts (e.g. lithium salt, sodium salt, potassium salt, magnesium salt or calcium salt), ammonium salts (e.g. ammonium salt, methylammonium salt, dimethylammonium salt, trimethylammonium salt, tetramethylammonium salt or dicyclohexylammonium salt), when basic groups are contained therein, are mineral acid salts (e.g. hydrochloride, bromide, sulfate, nitrate or phosphate), and organic acid salts (e.g. methanesulfonate, benzenesulfonate, p-toluenesulfonate, acetate, propionate, tartrate, fumarate, maleate, malate, oxalate, succinate, citrate, benzoate, mandelate, lactate or trifluoroacetate).

The amino compounds of Formula (1) of the present invention can exist independently in (R)-, (S)- or (RS)-form regarding the stereochemistry of asymmetric carbon atoms, and can exist in (E)-, (Z)- or (EZ)-form regarding the stereochemistry of the double bonds.

Methods for preparing the compounds of the present invention are illustrated as follows. For example, the above amino compounds can be prepared by the following methods.

[Method A]

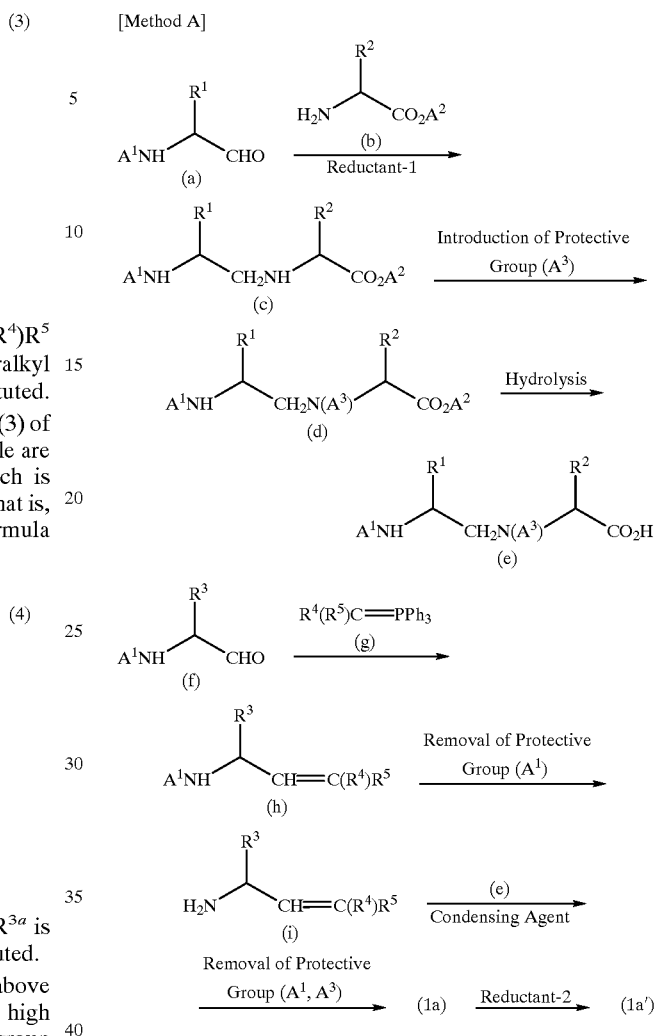

wherein $R^1-R^5$ are as defined above, $A^1$ and $A^3$ are each an amino-protective group, and $A^2$ is a carboxyl-protective group.

That is, an aldehyde (a) is reacted with an amino acid (b), followed by reduction to give an amino derivative (c). Subsequently, an amino-protective group is introduced, and hydrolysis gives a carboxylic acid (e). On the other hand, an aldehyde derivative (f) is reacted with a ylide (g) to give an alkene derivative (h). The protective group of the alkene derivative (h) is removed to give a compound (i), with which a carboxylic acid (e) is reacted using a condesing agent, followed by removal of the amino-protective group, thereby an amino compound (1a) of the present invention can be obtained. In addition, the amino compound (1a) is reduced to give an amino compound (1a') of the present invention.

[Method B]

$$A^1NH\overset{R^1}{\underset{}{\diagdown}}CONH\overset{R^2}{\underset{}{\diagdown}}CO_2A^2 \xrightarrow{\text{Reductant-3}}$$
(j)

-continued

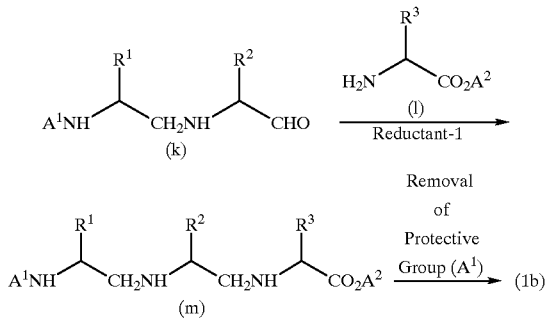

wherein $R^1$–$R^3$, $A^1$ and $A^2$ are as defined above.

That is, an aldehyde (k) obtained by reduction of a dipeptide (j) is reacted with an amino acid (l), followed by treating with a reductant-3 to give an amino derivative (m). The amino-protective group of the amino derivative (m) is removed, and thereby an amino compound (1b) of the present invention is obtained.

[Method C]

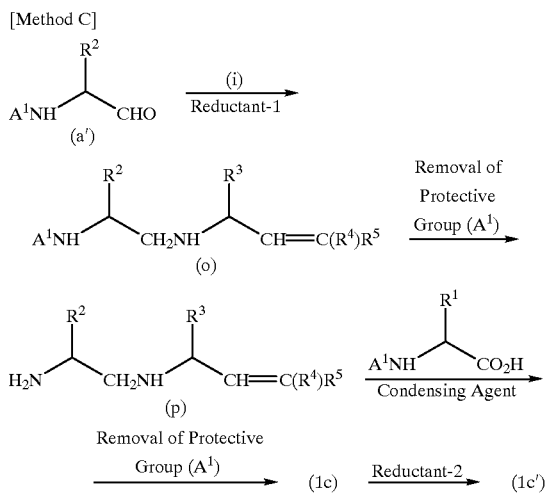

wherein $R^1$–$R^5$ and $A^1$ are as defined above.

That is, an aldehyde derivative (a') is reacted with an amino derivative (i), followed by treating with a reactant-1 to give a amino derivative (o). The amino-protective group of the amino derivative (o) is removed, and the resulting compound (p) is reacted with an amino acid using a condensing agent, followed by removal of the amino-protective group to give an amino compound (1c) of the present invention. In addition, reduction of the amino compound (1c) gives an amino compound (1c') of the present invention.

An ester derivative (d) is reacted with a reductant-3 and an amino derivative (i), successively, and then treated with a reductant-1 to give a diamino derivative (q). The amino-protective groups of the diamino derivative (q) are removed to give an amino compound (1d) of the present invention. In addition, the amino compound (1d) is treated with a reductant-2 to give an amino compound (1d') of the present invention.

In the methods for preparing the compounds of the present invention, examples of the reductant-1 are metal hydrides (e.g. sodium cyanoborohydride, lithium cyanoborohydride, sodium borohydride or lithium aluminum hydride) or dimethylamine-boran complex. The amount of the reductant-1 is about 1 to 5 equivalents. The reductant-2 means catalytic hydrogenation in the presence of a catalyst. Examples of the catalyst to be used herein are palladium, palladium-black, palladium-carbon, platinum, platinum oxide and rhodium. The sufficient amount of the catalyst is about 0.0001 to 1 equivalent. Examples of the reductant-3 are aluminum diisobutyl hydride, sodium aluminum hydride and aluminum tri-tert-butoxy hydride, and the amount of the reductant-3 is about 1 to 5 equivalents.

Examples of the solvent to be used in the reactions using these reductants are aromatic hydrocarbons (e.g. toluene or benzene), ethers (e.g. tetrahydrofuran, dioxane, diethyl ether or diisopropyl ether), halogenated hydrocarbons (e.g. dichloromethane, dichloroethane or chloroform), methanol, ethanol, water and a mixture thereof. Any other reaction-inert solvents may be used as well. The reaction temperature is from –78 to 200° C., and the reaction time is from 0.5 to 24 hours.

In the methods for preparing the compounds of the present invention, examples of the amino-protective group are groups easily removable by acid hydrolysis or hydrogenation (e.g. a benzyloxycarbonyl group, a tert-butoxycarbonyl group, a formyl group, a chloroacetyl group, a trityl group, a trialkylsilyl group, an acetamidomethyl group, a benzyl group, a 9-fluorenylmethoxycarbonyl group), and examples of the carboxyl-protective group are a methyl group, an ethyl group, a benzyl group and a phenacyl group.

As the condensation reactions and reagents to be used for the above methods, preferred examples are a method using N,N'-dicyclohexylcarbodiimide or N,N'-dicyclohexylcarbodiimide with 1-hydroxybenzotriazole, a method using 1-ethyl-3-(3-dimethylaminopropyl) carbodiimide with 1-hydroxybenzotriazole, a method using 1-ethyl-3-(3-dimethylaminopropyl)carbodiimide with 3-hydroxy-3,4-dihydro-4-oxo-1,2,3-benzotriazine, or a method using isobutyl chloroformate or diphenylphosphoryl azide in the presence of 1,1'-carbonyldiimidazole or triethylamine.

The protective groups can be removed according to the methods described in literatures, for example, hydrolysis

[Method D]

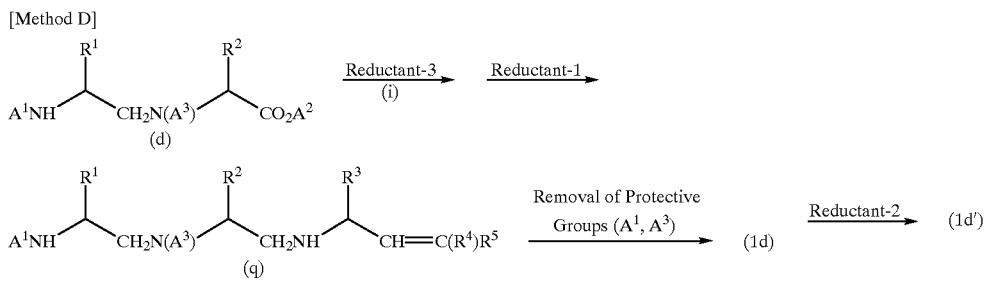

using mineral acids (e.g. hydrofluoric acid, hydrochloric acid or hydrobromic acid), or organic acids (e.g. trifluoroacetic acid), or alkali hydroxides (e.g. sodium hydroxide or barium hydroxide) or hydrogenation in the presence of palladium metal compounds (T. W. Greene et al., Protective Groups in Organic Synthesis, John Wiley & Sons, Inc., New York, 1911, pp. 14–142, pp. 397–405).

According to the methods for preparing the compounds of the present invention, it is preferable to use a solvent in the condensation reactions, the introduction or removal reactions of the protective group, or a Wittig reaction. Examples of the solvent are water, alcohols (e.g. methanol, ethanol or isopropanol), organic acids (e.g. acetic acid or propionic aid), esters (e.g. methyl acetate or ethyl acetate), ethers (e.g. diisopropyl ether, tetrahydrofuran, dioxane or anisole), aromatic hydrocarbons (e.g. benzene or toluene), halogenated hydrocarbons (e.g. dichloromethane or dichloroethane), ketones (e.g. acetone or ethylmethylketone), aprotic polar solvents (e.g. dimethyl sulfoxide or N,N-dimethylformamide) or a mixture thereof. Any other reaction-inert solvents may be used as well. The reaction temperature is from −78 to 200° C., and especially, the condensation reaction is preferably carried out at −30 to 50° C., and removal of the protective group is preferably carried out at −30 to 100° C., the Wittig reaction is preferably carried out at −78 to 50° C.

BEST MODE FOR CARRYING OUT THE INVENTION

The present invention is illustrated in more detail by the following Reference Examples, Examples and Test Examples, which are not intended to limit the scope of the present invention.

REFERENCE EXAMPLE 1

Preparation of N-(tert-butoxycarbonyl)-N-[(S)-2-(tert-butoxycarbonylamino)hexyl]-L-tyrosine

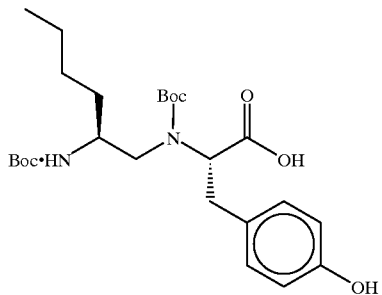

(1) Under an argon gas stream, N-(tert-butoxycarbonyl)-L-norleucine methyl ester (10.7 g, 38 mmol) was dissolved in toluene (68 ml), and cooled to −78° C. To the solution, while keeping the temperature at −60 to −70° C., was added gradually aluminum diisobutyl hydride (toluene 1.0 M solution, 51 ml). After stirring at −78° C. for an hour, the cooling bath was removed, methanol (2 ml) was added to the mixture. Tyrosine methyl ester hydrochloride (13.6 g, 59 mmol) and acetic acid (3.5 g, 59 mmol) were dissolved in methanol (69 ml)-tetrahydrofuran (98 ml), and added to the mixture. After addition of a suspension of sodium cyanoborohydride (2.7 g, 43 mmol) in tetrahydrofuran (30 ml), the mixture was stirred at room temperature for 2.5 hours, and water was added thereto. The solid was removed by decantation, and the solution was concentrated under reduced pressure. The organic matters were extracted with ethyl acetate, and washed with a saturated aqueous sodium bicarbonate solution, water and a saturated aqueous sodium chloride solution, successively. The organic layer was concentrated under reduced pressure and purified by column chromatography to give N-[(S)-2-(tert-butoxycarbonylamino)hexyl]-L-tyrosine methyl ester (4.9 g).

$^1$H-NMR(CDCl$_3$, 200 MHz) δ (ppm); 0.85(t, J=6.3 Hz, 3H), 1.08–1.52(m, 6H), 1.44(s, 9H), 2.45(dd, J=6.3, 11.9 Hz, 1H), 2.65(dd, J=5.0, 11.9 Hz, 1H), 2.81(dd, J=6.8, 13.4 Hz, 1H), 2.90(dd, J=6.2, 13.4 Hz, 1H), 3.33–3.65(m, 4H), 3.66 (s, 3H), 4.60(m, 1H), 6.72(d, J=8.4 Hz, 2H), 7.00(d, J=8.4 Hz, 2H)

(2) N-[(S)-2-(tert-Butoxycarbonylamino)hexyl]-L-tyrosine methyl ester (4.8 g, 12 mmol) was dissolved in 1,4-dioxane (50 ml), and di-tert-butyl dicarbonate (5.2 g, 24 mmol) was added thereto, followed by heating at 80° C. for 8 hours. After cooling, the organic layer was concentrated under reduced pressure, and purified by column chromatography to give by N-(tert-butoxycarbonyl)-N-[(S)-2-(tert-butoxycarbonylamino)hexyl]-L-tyrosine methyl ester (5.9 g).

$^1$H-NMR(DMSO-d$_6$, 400 MHz) δ (ppm); 0.77–0.89(m, 3H), 0.89–1.29(m, 6H), 1.33(s, 9H), 1.37(s, 9H), 2.70–3.36 (m, 5H), 3.57–3.67(m, 3H), 4.08(m, 1H), 6.31(m, 1H), 6.65(d, J=7.8 Hz, 2H), 6.99(d, J=7.8 Hz, 2H), 9.18(s, 1H)

(3) N-(tert-Butoxycarbonyl)-N-[(S)-2-(tert-butoxycarbonylamino)hexyl]-L-tyrosine methyl ester (4.9 g, 10 mmol) was dissolved in methanol (100 ml), and an aqueous 2M-sodium hydroxide solution was added thereto under ice-cooling. After stirring at room temperature for 4 hours, the mixture was made acidic with 2M-hydrochloric acid. After concentration under reduced pressure, the organic matters were extracted with chloroform, and washed with a saturated aqueous sodium chloride solution. The organic layer was dried over anhydrous sodium sulfate, and the solvent was evaporated under reduced pressure to give the title compound (4.7 g).

$^1$H-NMR(DMSO-d$_6$, 200 MHz) δ (ppm); 0.84(t, J=6.3 Hz, 3H), 0.98–1.50(m, 2H), 2.57–3.22(m, 4H), 3.72(m, 1H), 4.00–4.48(m, 1H), 6.53–6.70(m, 2H), 6.90(d, J=8.2 Hz, 2H), 8.10–8.65(m, 1H), 9.03–9.30(m, 1H)

REFERENCE EXAMPLE 2

Preparation of (3S,4S)-(E)-4-methyl-1-(4-methylphenyl)-1-hexen-3-amine hydrochloride

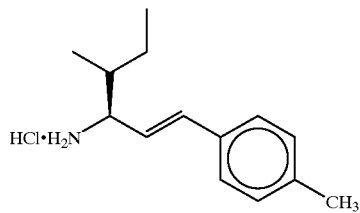

(1) To a solution of pyridine—sulfur trioxide complex (5.1 g, 32 mmol) in dimethyl sulfoxide (20 ml)—dichloromethane (20 ml) was added dropwise a solution of (S)-N-(tert-butoxycarbonyl)-isoleucinol (1.4 g, 6.5 mmol) and triethylamine (3.2 g, 32 mmol) in dimethyl sulfoxide (20 ml)—dichloromethane (20 ml) under an argon gas stream and ice-cooling. After stirring for 30 minutes, the reaction solution was poured into water, and extracted with dichloromethane. The organic layer was washed with a saturated aqueous citric acid solution, an aqueous sodium bicarbonate solution, water and an aqueous sodium chloride solution, successively. After drying over sodium sulfate, the solvent was evaporated under reduced pressure to give (2S,3S)-2-(tert-butoxycarbonylamino)-3-methylpentanal (1.3 g).

(2) To a suspension of (4-methylphenyl) methyltriphenylphosphonium chloride (4.8 g, 12 mmol) in ether (60 ml) was added dropwise n-butyl lithium (1.6 M hexane solution, 7.5 ml) under an argon gas stream at room temperature, followed by stirring for 3 hours. To the reaction solution was added a solution of (2S,3S)-2-(tert-butoxycarbonylamino)-3-methylpentanal (1.3 g, 6.0 mmol) in ether (10 ml). After the reaction, the reaction solution was poured into ice-water, extracted with ethyl acetate and washed with water and an aqueous sodium chloride solution, successively. The solution was concentrated under reduced pressure, and the residue was purified by column chromatography to give (3S,4S)-(E)-N-(tert-butoxycarbonyl)-4-methyl-i-(4-methylphenyl)-1-hexen-3-amine (1.0 g).

$^1$H-NMR(CDCl$_3$, 200 MHz) δ (ppm); 0.90(d, J=6.6 Hz, 3H), 0.93(t, J=7.2 Hz, 3H), 1.00–1.70(m, 3H), 1.45(s, 9H), 2.33(s, 3H), 4.21(m, 1H), 4.60(m, 1H), 6.02(dd, J=6.7, 15.9 Hz, 1H), 6.47(d, J=15.9 Hz, 1H), 7.11(d, J=8.1 Hz, 2H), 7.27(d, J=8.1 Hz, 2H)

(3) Under an argon gas stream, (3S,4S)-(E)-N-(tert-butoxycarbonyl)-4-methyl-1-(4-methylphenyl)-1-hexen-3-amine (1.00 g, 3.3 mmol) was dissolved in ethyl acetate (13 ml), and then a solution of 4M-hydrochloric acid in ethyl acetate (8.3 ml) was added thereto under ice-cooling. After stirring at room temperature for 3 hours, evaporation of the solvent under reduced pressure gave the title compound (0.73 g).

$^1$H-NMR(DMSO-d$_6$, 200 MHz) δ (ppm); 0.89(t, J=7.4 Hz, 3H) 0.92(d, J=6.8 Hz, 3H), 1.15(m, 1H), 1.42(m, 1H), 1.85(m, 1H), 2.29(s, 3H), 3.75(dd, J=5.2, 8.2 Hz, 1H), 6.13(dd, J=8.2, 16.0 Hz, 1H), 6.68(d, J=1 6.0 Hz, 1H), 7.18(d, J=8.0 Hz, 2H), 7.34(d, J=8.0 Hz, 2H), 8.35(br, 3H)

REFERENCE EXAMPLE 3

Preparation of (3S,4S)-(Z)-3-methyl-5-nonen-4-amine hydrochloride

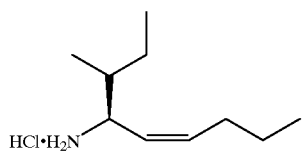

The title compound was obtained from butyltriphenylphosphonium bromide and (2S,3S)-2-(tert-butoxycarbonylamino)-3-methylpentanal in the same manners as in Reference Example 2 (2) and (3).

$^1$H-NMR(CDCl$_3$, 200 MHz) δ (ppm); 0.70–1.10(m, 9H), 1.20–2.30(m, 7H), 3.92(dd, J=5.4, 10.7 Hz, 1H), 5.46(dd, J=10.7, 10.7 Hz, 1H), 5.75(dt, J=10.7, 7.4 Hz, 1H), 8.43(br, 3H)

REFERENCE EXAMPLE 4

Preparation of (S)-(E)-6-methyl-1-phenyl- 2-hepten-4-amine hydrochloride

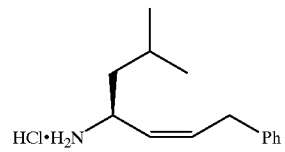

The title compound was obtained from (2-phenylethyl) triphenylphosphonium bromide and (S)-2-(tert-butoxycarbonylamino)-4-methylpentanal in the same manners as in Reference Example 2 (2) and (3).

$^1$H-NMR(DMSO-d$_6$, 200 MHz) δ (ppm); 0.86(d, J=6.4 Hz, 3H), 0.89(d, J=6.4 Hz, 3H), 1.35–1.73(m, 3H), 3.48(d, J=7.5 Hz, 2H), 4.12(m, 1H), 5.40(dd, J=10.7, 10.7 Hz, 1H), 5.83(dt, J=10.7, 7.5 Hz, 1H), 7.15–7.40(m, 5H), 8.20(br, 3H)

REFERENCE EXAMPLE 5

Preparation of (S)-(E)-1-(4-methoxycarbonylphenyl)-5-methyl-1-hexen-3-amine hydrochloride

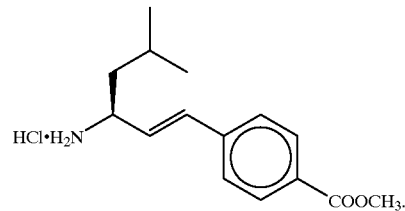

The title compound was obtained from (4-methoxycarbonylphenyl)methyltriphenylphosphonium bromide and (S)-2-(tert-butoxycarbonylamino)-4-methylpentanal in the same manners as in Reference Example 2 (2) and (3).

$^1$H-NMR(CDCl$_3$, 200 MHz) δ (ppm) 0.77–1.00(m, 6H), 1.36–1.76(m, 3H), 3.85(s, 3H), 3.88(m, 1H), 6.34(dd, J=8.3, 16.0 Hz, 1H), 6.97(d, J=16.0 Hz, 1H), 7.60(d, J=8.3 Hz, 2H), 7.96(d, J=8.3H, 2H), 8.20(br, 3H)

REFERENCE EXAMPLE 6

Preparation of (S)-(E)-1-(1-naphthyl)-5-methyl-1-hexen-3-amine hydrochloride

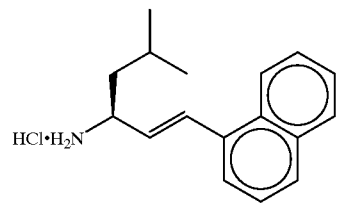

(1) Under an argon gas stream, N-(tert-butoxycarbonyl)-L-leucine methyl ester (0.98 g, 4.0 mmol) was dissolved in toluene (7.1 ml), and cooled to −78° C. To the reaction solution, while keeping the temperature at −60 to −70° C., was added gradually aluminum diisobutyl hydride (toluene 1.0 M solution, 5.0 ml). After stirring at −78° C. for 30 minutes, thereby there was obtained (S)-2-(tert-butoxycarbonylamino)-4-methylpentanal.

(2) To a suspension of (1-naphthylmethyl) triphenylphosphonium chloride (3.4 g, 8.0 mmol) in tetrahydrofuran (30 ml) was added dropwise lithium bis (trimethylsilyl)amide (tetrahydrofuran 1.0 M solution, 8.0 ml) under an argon gas stream and ice-cooling, followed by stirring at room temperature for 2 hours. The reaction solution was cooled to −70° C., and a solution of (S)-2-(tert-butoxycarbonylamino)-4-methylpentanal (corresponding to 4.0 mmol) obtained in the above (1) was added thereto. After the reaction, methanol (0.21 ml) and an aqueous potassium sodium tartrate solution [the saturated solution (2.7 ml) and water (13 ml)] were added to the reaction solution. The reaction solution was extracted with ethyl acetate, and washed with water and an aqueous sodium chloride solution, successively. After evaporation of the solvent under reduced pressure, purification by column chromatography gave (S)-(E)-N-(tert-butoxycarbonyl)-5-methyl-1-(1-naphthyl)-1-hexen-3-amine (0.53 g).

$^1$H-NMR(CDCl$_3$, 200 MHz) δ (ppm); 1.00(d, J=6.5 Hz, 6H), 1.35–1.68(m, 2H), 1.49(s. 9H), 1.77(m, 1H), 4.32–4.68 (m, 2H), 6.07(dd, J=6.3, 15.6 Hz, 1H), 7.27(d, J=15.6 Hz, 1H), 7.36–7.65(m, 4H), 7.70–7.90(m, 2H), 8.11(m, 1H)

(3) The title compound was obtained from (S)-(E)-N-(tert-butoxycarbonyl)-5-methyl-1-(1-naphthyl)-1-hexen-3-amine in the same manner as in Reference Example 2(3).

$^1$H-NMR(DMSO-d$_6$, 200 MHz) δ (ppm); 0.95(d, J=5.8 Hz, 3H), 0.96(d, J=5.8 Hz, 3H), 1.50–1.87(m, 3H), 4.02(m, 1H), 6.21(dd, J=8.2, 15.8 Hz, 1H), 7.45–7.75(m, 5H), 7.86–8.03(m, 2H), 8.17–8.49(m, 4H)

REFERENCE EXAMPLE 7

Preparation of (S)-(E)-5-methyl-1-phenyl-1-hexen-3-amine hydrochloride

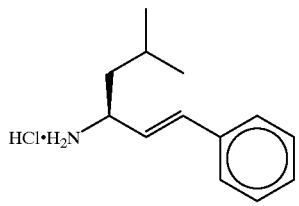

(1) Under an argon gas stream, N-(tert-butoxycarbonyl)-(L)-leucine methyl ester (9.8 g, 40 mmol) as dissolved in toluene (70 ml), and cooled to −78° C. To the solution, while keeping the temperature at −60 to −70° C., was added gradually aluminum diisobutyl hydride (toluene 1.0 M solution, 52 ml). After stirring at −78° C. for 40 minutes, the cooling bath was removed, and methanol (2.1 ml) and 20% aqueous citric acid solution (30 ml) were added to the mixture, followed by extraction with ethyl acetate. The organic layer was washed with 20% aqueous citric acid solution, a saturated aqueous sodium bicarbonate solution, water and a saturated aqueous sodium chloride solution, successively. The organic layer was dried over anhydrous sodium sulfate, and the solvent was evaporated under reduced pressure to give (S)-2-(tert-butoxycarbonylamino)-5-methylpentanal (8.5 g).

(2) The title compound was obtained from benzyltriphenylphosphonium chloride and (S)-2-(tert-butoxycarbonylamino)-4-methylpentanal obtained in the above (1) in the same manners as in

REFERENCE EXAMPLE 2 (2) and (3)

$^1$H-NMR(CDCl$_3$, 200 MHz), δ (ppm); 0.85(d, J=6.0 Hz, 3H), 0.87(d, J=6.1 Hz, 3H), 1.50–1.90(m, 3H), 3.88(m, 1H), 6.15(dd, J=8.5, 15.9 Hz, 1H), 6.72(d, J=15.9 Hz, 1H), 7.18–7.46(m, 5H), 8.56(br, 3H)

REFERENCE EXAMPLE 8

Preparation of (E)-5-methyl-1-(4-pyridyl)-1-hexen-3-amine dihydrochloride

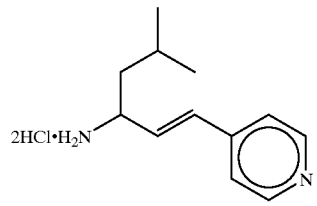

The title compound was obtained from (4-pyridylmethyl) triphenylphosphonium chloride and 2-(tert-butoxycarbonylamino)-4-methylpentanal synthesized in the same manner as in Reference Example 2(1) in the same manners as in Reference Example 2(2) and (3).

$^1$H-NMR(DMSO-d$_6$, 200 MHz) δ (ppm); 0.91(d, J=4.9 Hz, 6H), 1.50–1.76(m, 3H), 3.96(m, 1H), 6.84(dd, J=8.0, 16.1 Hz, 1H), 7.01(d, J=16.1 Hz, 1H), 7.99(d, 6.6 Hz, 2H), 8.68(br, 3H), 8.83(d, J=6.6 Hz, 2H)

REFERENCE EXAMPLE 9

Preparation of (S)-1-(4-chlorophenyl)-5-methyl-1-hexen-3-amine hydrochloride

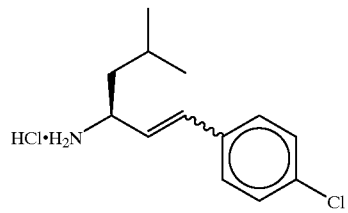

(S)-1-(4-Chlorophenyl)-5-methyl-1-hexen-3-amine hydrochloride (E:Z=3.3:1) was obtained from (4-chlorophenyl)methyltriphenylphosphonium chloride and (S)-2-(tert-butoxycarbonylamino)-4-methylpentanal obtained in Reference Example 7(1) in the same manners as in Reference Example 2(2) and (3). Recrystallization from chloroform and ethanol gave the title compound as the (E)-form thereof and a mixture of the (E)-form and the (Z)-form thereof (1:1).

(E)-form: $^1$H-NMR(CDCl$_3$, 200 MHz) δ (ppm); 0.85(d, J=5.9 Hz, 3H), 0.88(d, J=5.9 Hz, 3H), 1.50–1.86(m, 3H), 3.88(m, 1H), 6.12(dd, J=8.4, 15.9 Hz, 1H), 6.67(d, J=15.9 Hz, 1H), 7.21(d, J=8.8 Hz, 2H), 7.27(d, J=8.8 Hz, 2H), 8.54(br, 3H)

REFERENCE EXAMPLE 10

Preparation of (S)-(E)-1-([1,1'-biphenyl]-4-yl)-5-methyl-1-hexen-3-amine hydrochloride

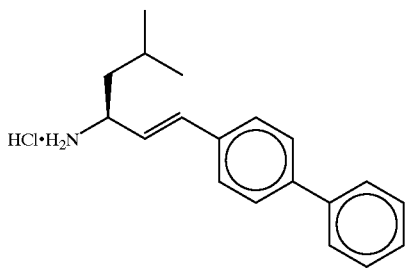

The title compound was obtained from [1,1'-biphenyl]-4-ylmethyltriphenylphosphonium chloride and (S)-2-(tert-butoxycarbonylamino)-4-methylpentanal obtained in Reference Example 7(1) in the same manners as in Reference Example 2(2) and (3).

$^1$H-NMR(CDCl$_3$, 200 MHz) δ (ppm); 0.86(d, J=5.8 Hz, 3H), 0.89(d, J=6.0 Hz, 3H), 1.39–1.88(m, 3H), 3.94(m, 1H), 6.22(dd, J=8.4, 15.9 Hz, 1H), 6.79(d, J=15.9 Hz, 1H), 7.20–7.60(m, 9H), 8.62(br, 3H)

REFERENCE EXAMPLE 11

Preparation of (S)-(E)-1-(2-quinolyl)-5-methyl-1-hexen-3-amine dihydrochloride

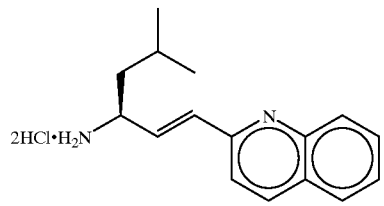

The title compound was obtained from (2-quinolylmethyl)triphenylphosphonium chloride and (S)-2-(tert-butoxycarbonylamino)-4-methylpentanal in the same manner as in Reference Example 6.

$^1$H-NMR(DMSO-d$_6$, 200 MHz) δ (ppm); 0.93(d, J=5.7 Hz, 6H), 1.45–1.83(m, 3H), 4.03(m, 1H), 7.07(dd, J=7.5, 16.1 Hz, 1H), 7.18(d, J=16.1 Hz, 1H), 7.71(m, 1H), 7.81–8.02(m, 2H), 8.10(d, J=8.5 Hz, 1H), 8.18(d, J=8.5 Hz, 1H), 8.46(br, 3H), 8.65(d, J=8.5 Hz, 1H)

REFERENCE EXAMPLE 12

Preparation of (S)-5-methyl-1-hexen-3-amine hydrochloride

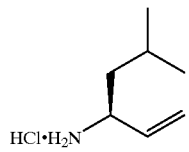

The title compound was obtained from methyltriphenylphosphonium iodide and (S)-2-(tert-butoxycarbonylamino)-4-methylpentanal in the same manner as in Reference Example 7.

$^1$H-NMR(CDCl$_3$, 200 MHz) δ (ppm); 0.91(d, J=6.1 Hz, 3H), 0.95(d, J=7.0 Hz, 3H), 1.50–2.00(m, 2H), 3.77(m, 1H), 5.37(d, J=10.1 Hz, 1H), 5.40(d, J=17.0 Hz, 1H), 5.87(ddd, J=7.8, 10.1, 17.0 Hz, 1H), 8.50(br, 3H)

REFERENCE EXAMPLE 13

Preparation of (S)-(E)-N-[(S)-2-amino-3-(4-hydroxyphenyl)propyl]-5-methyl-1-phenyl-1-hexen-3-amine dihydrochloride

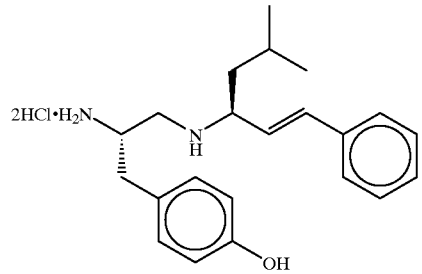

(1) (S)-(E)-N-[(S)-2-(tert-Butoxycarbonylamino)-3-(4-hydroxyphenyl)propyl]-5-methyl-1-phenyl-1-hexen-3-amine was obtained from N-(tert-butoxycarbonyl)-L-tyrosine methyl ester and (S)-(E)-5-methyl-1-phenyl-1-hexen-3-amine hydrochloride in the same manner as in Reference Example 1(1).

$^1$H-NMR(CDCl$_3$, 200 MHz) δ (ppm); 0.87(d, J=6.3 Hz, 3H), 0.90(d, J=6.3 Hz, 3H), 1.29–1.48(m, 3H), 1.40(s, 9H), 1.62(m, 1H), 2.51(dd, J=6.4, 12.3 Hz, 1H), 2.59–2.85(m, 3H), 3.17(m, 1H), 3.81(m, 1H), 4.70(m, 1H), 5.91(dd, J=8.5, 15.9 Hz, 1H), 6.41(d, J=15.9 Hz, 1H), 6.64(d, J=8.5 Hz, 2H), 6.97(d, 8.5 Hz, 2H), 7.15–7.43(m, 5H)

(2) The title compound was obtained from (S)-(E)-N-[(S)-2-(tert-butoxycarbonylamino)-3-(4-hydroxyphenyl)propyl]-5-methyl-1-phenyl-1-hexen-3-amine in the same manner as in Reference Example 2(3).

$^1$H-NMR(DMSO-d$_6$, 200 MHz) δ (ppm); 0.89(d, J=6.5 Hz, 6H), 1.42–1.84(m, 3H), 2.78(dd, J=8.0, 14.4 Hz, 1H), 2.90(dd, J=6.4, 14.4 Hz, 1H), 2.94–3.28(m, 2H), 3.69(m, 1H), 3.84(m, 1H), 6.05(dd, J=9.4, 16.0 Hz, 1H), 6.65(d, J=8.3 Hz, 2H), 6.82(d, J=16.0 Hz, 1H), 7.02(d, J=8.3 Hz, 2H), 7.24–7.49(m, 5H), 8.50(br, 3H), 9.39(s, 1H), 9.50(br, 1H), 9.84(br, 1H)

EXAMPLE 1

Preparation of N'-[(S)-2-aminohexyl]-N-[(S)-(E)-3-(4-methylphenyl)-1-[(S)-1-methylpropyl]- 2-propenyl]-L-tyrosinamide dihydrochloride

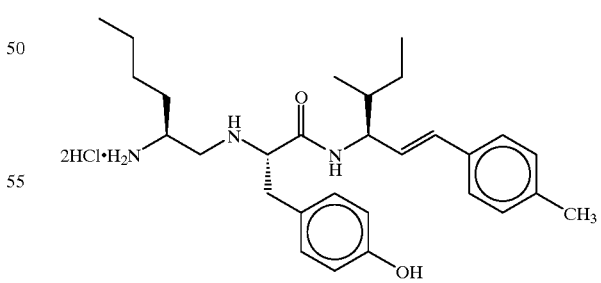

(1) Under an argon gas stream, N-(tert-butoxycarbonyl)-N-[(S)-2-(tert-butoxycarbonylamino)hexyl]-L-tyrosine (384 mg, 0.80 mmol) and 1-hydroxybenzotriazole monohydrate (135 mg, 0.88 mmol) were dissolved in tetrahydrofuran (8.0 ml), and N,N'-dicyclohexylcarbodiimide (181 mg, 0.88 mmol) was added thereto. After stirring at room temperature for an hour, a suspension of (3S,4S)-(E)-4-methyl-1-(4- methylphenyl)-1-hexen-3-amine hydrochloride (192 mg, 0.80 mmol) and triethylamine (161 mg, 1.6 mmol) in tetrahydrofuran (3.0 ml) was added to the reaction solution, followed by stirring for 15 hours. After the reaction, the insoluble matters were filtered off, and the solvent was evaporated under reduced pressure. The residue was extracted with ethyl acetate, and the organic layer was washed with 1 M hydrochloric acid, a saturated aqueous sodium bicarbonate solution, water and a saturated aqueous sodium chloride solution, successively. After drying over anhydrous sodium sulfate, evaporation of the solvent under reduced pressure gave N'-(tert-butoxycarbonyl)-N'-[(S)-2-(tert-butoxycarbonylamino)hexyl]-N-[(S)-(E)-3-(4-methylphenyl)-1-[(S)-1-methylpropyl]-2-propenyl]-L-tyrosinamide (380 mg).

(2) The title compound was obtained from N'-(tert-butoxycarbonyl)-N'-[(S)-2-(tert-butoxycarbonylamino)hexyl]-N-[(S)-(E)-3-(4-methylphenyl)-1-[(S)-1-methylpropyl]-2-propenyl]-L-tyrosinamide in the same manner as in Reference Example 2(3).

$^1$H-NMR(DMSO-$d_6$, 400 MHz) δ (ppm); 0.78–0.94(m, 9H), 1.12(m, 1H), 1.17–1.35(m, 4H), 1.41(m, 1H), 1.48–1.68(m, 3H), 2.29(s, 3H), 2.70–3.63(m, 5H), 4.12(m, 1H), 4.33(m, 1H), 5.97(dd, J=5.9, 16.0 Hz, 1H), 6.11(d, J=16.0 Hz, 1H), 6.61(d, J=8.4 Hz, 2H), 7.00(d, J=8.4 Hz, 2H), 7.14(d, J=8.1 Hz, 2H), 7.23(d, J=8.1 Hz, 2H), 8.30–8.90(m, 4H), 9.35(s, 1H), 9.50(br, 1H), 10.30(br, 1H) MASS(m/e): 465($M^+$)

EXAMPLE 2

Preparation of N'-[(S)-2-aminohexyl]-N-[(1R,2S)-2-methyl-1-[2-(4-methylphenyl)ethyl]butyl]-L-tyrosinamide dihydrochloride

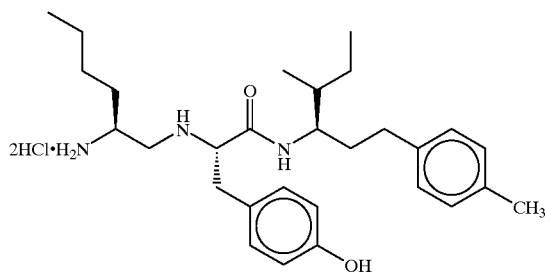

N'-[(S)-2-Aminohexyl]-N-[(S)-(E)-3-(4-methylphenyl)-1-[(S)-1-methylpropyl]-2-propenyl]-L-tyrosinamide dihydrochloride (93 mg, 0.17 mmol) was dissolved in methanol (2.0 ml), and then 10% palladium carbon (20 mg) was added to the solution. The mixture was stirred at room temperature under a hydrogen gas stream until the starting material was diminished. After removal of the solid, evaporation of the solvent under reduced pressure gave the title compound (90 mg).

$^1$H-NMR(DMSO-$d_6$, 400 MHz) δ (ppm); 0.70–0.98(m, 9H), 1.05(m, 1H), 1.15–1.80(m, 10H), 1.90–2.25(m, 2H), 2.67–3.65(m, 6H), 4.11(m, 1H), 6.67(d, J=8.1 Hz, 2H), 6.92(d, J=8.1 Hz, 2H), 7.20–7.34(m, 4H), 8.20–8.80(m, 4H), 9.07–10.37(br, 3H) MASS(m/e): 467($M^+$)

EXAMPLE 3

Preparation of N'-[(S)-2-aminohexyl]-N-[(S)-(Z)-1-[(S)-1-methylpropyl]-2-hexenyl]-L-tyrosinamide dihydrochloride

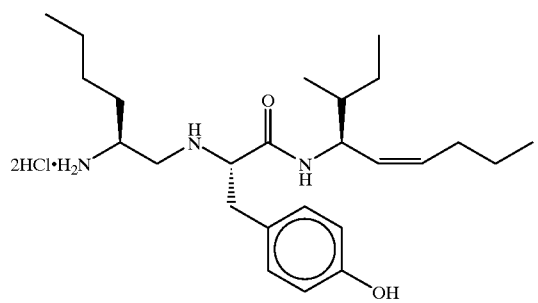

The title compound was obtained from N-(tert-butoxycarbonyl)-N-[(S)-2-(tert-butoxycarbonylamino)hexyl]-L-tyrosine and (3S,4S)-(Z)-3-methyl-5-nonen-4-amine hydrochloride in the same manner as in Example 1.

$^1$H-NMR(DMSO-$d_6$, 400 MHz) δ (ppm); 0.71–0.98(m, 12H), 1.05(m, 1H), 1.18–1.70(m, 10H), 1.93–2.10(m, 2H), 2.89–3.27(m, 4H), 3.49(m, 1H), 3.98(m, 1H), 4.40(m, 1H), 5.07(dd, J=10.8 Hz, 10.8 Hz, 1H), 5.45(dt, J=10.8 Hz, 7.3 Hz, 1H), 6.65(d, J=8.4 Hz, 2H), 6.97(d, J=8.4 Hz, 2H), 8.28–8.73(br, 4H), 9.18–9.62(br, 2H), 10.22(br, 1H) MASS (m/e): 509($M^+$)

EXAMPLE 4

Preparation of N'-[(S)-2-aminohexyl]-N-[(R)-1-[(S)-1-methylpropyl]hexyl]-L-tyrosinamide dihydrochloride

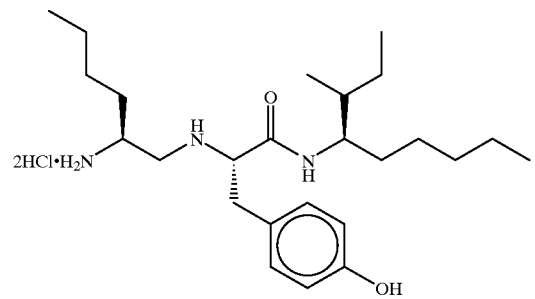

The title compound was obtained from N'-[(S)-2-aminohexyl]-N-[(S)-(Z)-1-[(S)-1-methylpropyl]-3-phenyl-2-hexenyl]-L-tyrosinamide dihydrochloride in the same hydrogenation as in Example 2.

$^1$H-NMR(DMSO-$d_6$, 400 MHz) δ (ppm); 0.77(d, J=6.8 Hz, 3H), 0.81(t, J=7.2 Hz, 3H), 0.87(d, J=6.7 Hz, 3H), 0.89(t, J=6.9 Hz, 3H), 0.98–1.73(m, 17H), 2.74–3.05(m, 2H), 3.05–3.66(m, 4H), 4.04(m, 1H), 6.67(d, J=8.4 Hz, 2H), 7.00(d, J=8.4 Hz, 2H), 8.27(br, 1H), 8.50(br, 3H), 9.30(br, 1H), 9.49(br, 1H), 10.23(br, 1H)

EXAMPLE 5

Preparation of N'-[(S)-2-aminohexyl]-N-[(S)-(Z)-1-(2-methylpropyl)-4-phenyl-2-butenyl]-L-tyrosinamide dihydrochloride

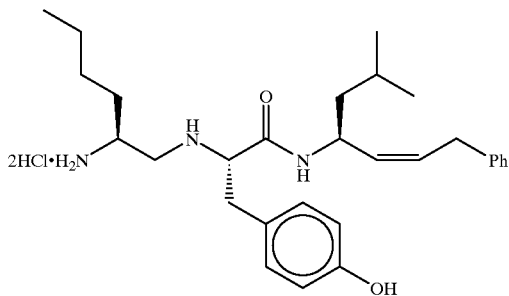

The title compound was obtained from N-(tert-butoxycarbonyl)-N-[(S)-2-(tert-butoxycarbonylamino)hexyl]-L-tyrosine and (S)-(Z)-6-methyl-1-phenyl-2-hepten-3-amine hydrochloride in the same manner as in Example 1.

$^1$H-NMR(DMSO-$d_6$, 400 MHz) δ (ppm); 0.85(d, J=6.4 Hz, 3H), 0.86(d, J=6.5 Hz, 3H), 0.87(t, J=6.8 Hz, 3H), 1.14–1.38(m, 5H), 1.38–1.70(m, 4H), 2.85–3.08(m, 2H), 3.08–3.28(m, 2H), 3.34–3.60(m, 3H), 3.95(br, 1H), 4.79(m, 1H), 5.11(dd, J=10.3, 10.3 Hz, 1H), 5.52(dt, J=10.3, 7.6 Hz, 1H), 6.63(d, J=8.4 Hz, 2H), 6.98(d, J=8.4 Hz, 2H), 7.10–7.40(m, 5H), 8.54(br, 3H), 8.62(br, 1H), 9.35(br, 1H), 9.46(br, 1H), 10.25(br, 1H) MASS(m/e): 465(M$^+$)

EXAMPLE 6

Preparation of N'-[(S)-2-aminohexyl]-N-[(R)-3-methyl-1-(3-phenylpropyl)butyl]-L-tyrosinamide dihydrochloride

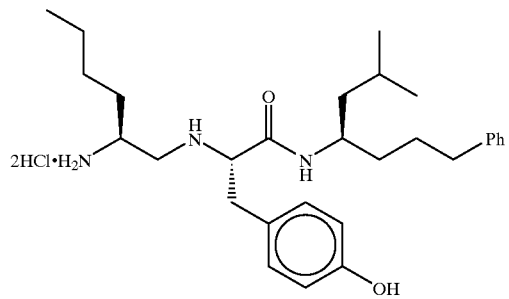

The title compound was obtained from N'-[(S)-2-aminohexyl]-N-[(S)-(Z)-1-(2-methylpropyl)-4-phenyl-2-butenyl]-L-tyrosinamide dihydrochloride in the same hydrogenation as in Example 2.

$^1$H-NMR(DMSO-$d_6$, 400 MHz) δ (ppm); 0.80(d, J=6.4 Hz, 3H), 0.81(d, J=6.4 Hz, 3H), 0.87(t, J=6.9 Hz, 3H), 1,01–1.38(m, 10H), 1.38–1.68(m, 3H), 2.36–2.48(m, 2H), 2.70–3.70(m, 5H), 3.78(m, 1H), 3.94(m, 1H), 6.68(d, J=8.4 Hz, 2H), 7.00(d, J=8.4 Hz, 2H), 7.09–7.21(m, 3H), 7.21–7.31(m, 2H), 8.26(br, 1H), 8.50(br, 3H), 9.40(br, 1H), 9.52(br, 1H), 10.25(br, 1H) MASS(m/e): 467(M$^+$)

EXAMPLE 7

Preparation of N'-[(S)-2-aminohexyl]-N-[(S)-(E)-1-(2-methylpropyl)-3-(4-pyridyl)-2-propenyl]-L-tyrosinamide trihydrochloride

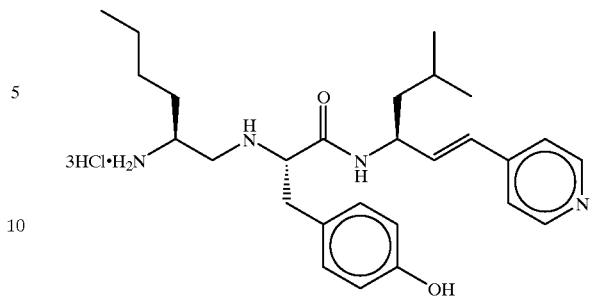

The title compound was obtained from N-(tert-butoxycarbonyl)-N-[(S)-2-(tert-butoxycarbonylamino)hexyl]-L-tyrosine and (S)-(E)-5-methyl-1-(4-pyridyl)-1-hexen-3-amine dihydrochloride in the same manner as in Example 1. $^1$H-NMR(DMSO-$d_6$, 400 MHz) δ (ppm); 0.88 (d, J=6.5 Hz, 3H), 0.89(t, J=6.5 Hz, 3H), 0.90(d, 6.5 Hz, 3H), 1.19–1.51(m, 6H), 1.52–1.71(m, 3H), 2.89(m, 1H), 2.94(dd, J=10.4, 13.5 Hz, 1H), 3.16–3.32(m, 2H), 3.52(m, 1H), 4.12(m, 1H), 4.57(m, 1H), 6.10(d, J=15.7 Hz, 1H), 6.62(dd, J=5.8, 15.7 Hz, 1H), 6.62(d, J=8.4 Hz, 2H), 7.01(d, J=8.4 Hz, 2H), 7.76(d, J=6.1 Hz, 2H), 8.60(br, 3H), 8.77(d, J=6.1 Hz, 2H), 8.90(d, J=8.4 Hz, 1H), 9.15–10.70(br, 2H), 9.43(br, 1H) MASS(m/e): 453(M$^+$+1)

EXAMPLE 8

Preparation of N'-[(S)-2-aminohexyl]-N-[(R)-3-methyl-1-[2-(4-pyridyl)ethyl]butyl]-L-tyrosinamide trihydrochloride

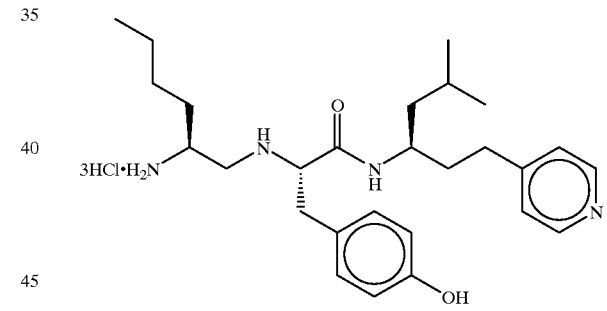

The title compound was obtained from N'-[(S)-2-aminohexyl]-N-[(S)-(E)-1-(2-methylpropyl)-3-(4-pyridyl)-2-propenyl]-L-tyrosinamide hydrochloride in the same hydrogenation as in Example 2.

$^1$H-NMR(DMSO-$d_6$, 400 MHz) δ (ppm); 0.82(d, J=6.2 Hz, 3H), 0.85(d, J=6.7 Hz, 3H), 0.88(t, J=6.9 Hz, 3H), 1.11–1.45(m, 7H), 1.45–1.73(m, 4H), 2.13(m, 1H), 2.30(m, 1H), 2.85(dd, J=2.4, 13.0 Hz, 1H), 2.91(dd, J=11.2, 13.0 Hz, 1H), 3.15–3.34(m, 2H), 3.51(m, 1H), 3.77(m, 1H), 4.11(m, 1H), 6.62(d, J=8.4 Hz, 2H), 7.05(d, J=8.4 Hz, 2H), 7.61(d, J=6.0 Hz, 2H), 8.63(br, 3H), 8.65(d, J=8.4 Hz, 1H), 8.75(d, J=6.0 Hz, 2H), 9.28(br, 1H), 10.25(br, 2H) MASS(m/e): 455(M$^+$+1)

EXAMPLE 9

Preparation of N'-[(S)-2-aminohexyl]-N-[(R)-(E)-1-(2-methylpropyl)-3-(4-pyridyl)-2-propenyl]-L-tyrosinamide trihydrochloride

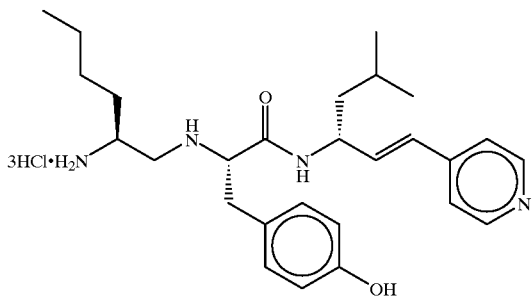

Carrying out the same reaction as in Example 1 using N-(tert-butoxycarbonyl)-N-[(S)-2-(tert-butoxycarbonylamino)hexyl]-L-tyrosine and (E)-5-methyl-1-(4-pyridyl)-1-hexen-3-amine dihydrochloride, followed by purification by column chromatography gave the title compound.

$^1$H-NMR(DMSO-d$_6$, 400 MHz) δ (ppm); 0.71(d, J=6.4 Hz, 3H), 0.75(d, J=6.7 Hz, 3H), 0.76(t, J=6.8 Hz, 3H), 1.10–1.32(m, 7H), 1.52–1.64(m, 2H), 2.93(dd, J=10.3, 13.1 Hz, 1H), 3.00(m, 1H), 3.18–3.28(m, 2H), 3.53(m, 1H), 4.11(m, 1H), 4.40(m, 1H), 6.70(d, J=8.5 Hz, 2H), 6.83(d, J=16.0 Hz, 1H), 6.95(dd, J=5.0, 16.0 Hz, 1H), 7.02(d, J=8.5 Hz, 2H), 8.02(d, J=5.8 Hz, 2H), 8.53(br, 3H), 8.72(d, J=7.7 Hz, 1H), 8.74(d, J=5.8 Hz, 2H), 9.37(br, 1H), 10.05(br, 2H) MASS(m/e): 453(M$^+$+1)

EXAMPLE 10

Preparation of N'-[(S)-2-aminohexyl]-N-[(S)-3-methyl-1-[2-(4-pyridyl)ethyl]butyl]-L-tyrosinamide trihydrochloride

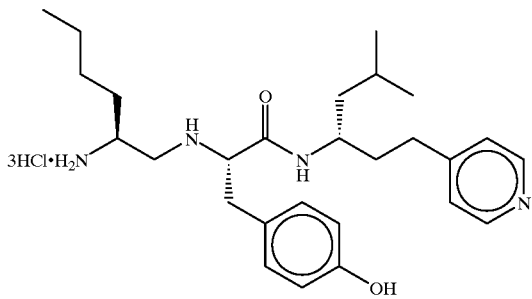

The title compound was obtained from N'-[(S)-2-aminohexyl]-N-[(R)-(E)-1-(2-methylpropyl)-3-(4-pyridyl)-2-propenyl]-L-tyrosinamide trihydrochloride according to the same hydrogenation as in Example 2.

$^1$H-NMR(DMSO-d$_6$, 400 MHz) δ (ppm); 0.66(d, J=6.3 Hz, 3H), 0.68(d, J=6.5 Hz, 3H), 0.81(t, J=7.0 Hz, 3H), 0.91(m, 1H), 0.96–1.15(m, 2H), 1.17–1.36(m, 4H), 1.56–1.80(m, 4H), 2.71–3.06(m, 4H), 3.15–3.34(m, 2H), 3.56(m, 1H), 3.69(m, 1H), 4.07(m, 1H), 6.68(d, J=8.5 Hz, 2H), 7.02(d, J=8.5 Hz, 2H), 7.89(d, J=6.3 Hz, 2H), 8.44(d, J=8.7 Hz, 1H), 8.62(br, 3H), 8.76(d, J=6.3 Hz, 2H), 9.30–10.68(br, 2H), 9.36(br, 1H) MASS(m/e): 455(M$^+$+1)

EXAMPLE 11

Preparation of N'-[(S)-2-aminohexyl]-N-[(S)-(E)-3-(4-methoxycarbonylphenyl)-1-(2-methylpropyl)-2-propenyl]-L-tyrosinamide dihydrochloride

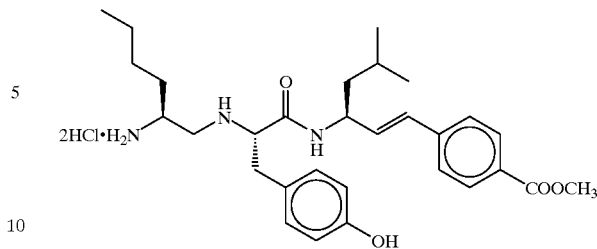

(1) N'-(tert-Butoxycarbonyl)-N'-[(S)-2-(tert-butoxycarbonylamino)hexyl]-N-[(S)-(E)-3-(4-methoxycarbonylphenyl)-1-(2-methylpropyl)-2-propenyl]-L-tyrosinamide was obtained from N-(tert-butoxycarbonyl)-N-[(S)-2-(tert-butoxycarbonylamino)hexyl]-L-tyrosine and (S)-(E)-1-(4-methoxycarbonylphenyl)-5-methyl-1-hexen-3-amine hydrochloride in the same manner as in Example 1(1).

(2) The title compound was obtained from N'-(tert-butoxycarbonyl)-N'-[(S)-2-(tert-butoxycarbonylamino)hexyl]-N-[(S)-(E)-3-(4-methoxycarbonylphenyl)-1-(2-methylpropyl)-2-propenyl]-L-tyrosinamide in the same manner as in Reference Example 2(3).

$^1$H-NMR(DMSO-d$_6$, 400 MHz) δ (ppm); 0.81–0.97(m, 9H), 1.01–1.70(m, 9H), 2.70–3.10(m, 2H), 3.10–3.70(m, 3H), 3.85(s, 3H), 4.04(m, 1H), 4.55(m, 1H), 6.03–6.22(m, 2H), 6.63(d, J=8.4 Hz, 2H), 7.01(d, J=8.4 Hz, 2H), 7.43(d, J=8.6 Hz, 2H), 7.92(d, J=8.6 Hz, 2H), 8.53(br, 3H), 8.70(br, 1H), 9.40(br, 1H), 9.57(br, 1H), 10.31(br, 1H) NASS(m/e): 509(M$^+$)

EXAMPLE 12

Preparation of N'-[(S)-2-aminohexyl]-N-[(R)-1-[2-(4-methoxycarbonylphenyl)ethyl]-3-methylbutyl]-L-tyrosinamide dihydrochloride

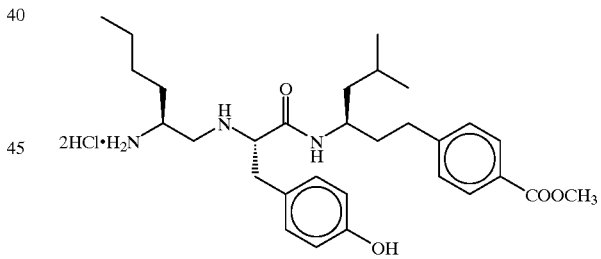

The title compound was obtained from N'-[(S)-2-aminohexyl]-N-[(S)-(E)-3-(4-methoxycarbonylphenyl)-1-(2-methylpropyl)-2-propenyl]-L-tyrosinamide dihydrochloride according to the same hydrogenation as in Example 2.

$^1$H-NMR(DMSO-d$_6$, 400 MHz) δ (ppm); 0.80(d, J=6.4 Hz, 3H), 0.82(d, J=6.4 Hz, 3H), 0.87(t, J=6.7 Hz, 3H), 1.20–1.75(m, 11H), 2.10–2.40(m, 2H), 2.68–3.00(m, 2H), 3.00–3.50(m, 3H), 3.77(m, 1H), 4.04(m, 1H), 6.67(d, J=8.0 Hz, 2H), 7.05(d, J=8.0 Hz, 2H), 7.19(d, J=8.1 Hz, 2H), 7.86(d, J=8.1 Hz, 2H), 8.48(br, 4H), 9.30(br, 1H), 9.58(br, 1H), 10.24(br, 1H) MASS(m/e): 511(M$^+$)

EXAMPLE 13

Preparation of N'-[(S)-2-aminohexyl]-N-[(S)-(E)-3-(4-carboxyphenyl)-1-(2-methylpropyl)-2-propenyl]-L-tyrosinamide dihydrochloride

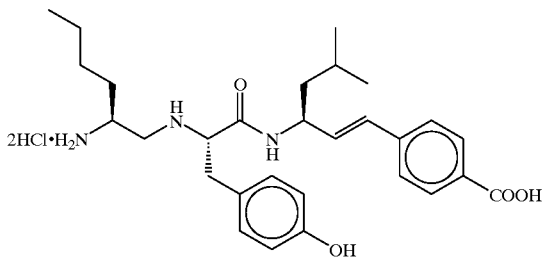

(1) N'-(tert-Butoxycarbonyl)-N'-[(S)-2-(tert-butoxycarbonylamino)hexyl]-N-[(S)-(E)-3-(4-carboxyphenyl)-1-(2-methylpropyl)-2-propenyl]-L-tyrosinamide was obtained from N'-(tert-butoxycarbonyl)-N'-[(S)-2-(tert-butoxycarbonylamino)hexyl]-N-[(S)-(E)-3-(4-methoxycarbonylphenyl)-1-(2-methylpropyl)-2-propenyl]-L-tyrosinamide in the same manner as in Reference Example 1(3), and then the title compound was obtained from N'-(tert-butoxycarbonyl)-N'-[(S)-2-(tert-butoxycarbonylamino)hexyl]-N-[(S)-(E)-3-(4-carboxyphenyl)-1-(2-methylpropyl)-2-propenyl]-L-tyrosinamide in the same manner as in Reference Example 2(3).

$^1$H-NMR(DMSO-d$_6$, 400 MHz) δ (ppm); 0.82–0.96(m, 9H), 1.01–1.68(m, 9H), 2.70–3.10(m, 2H), 3.10–3.60(m, 3H), 4.05(m, 1H), 4.52(m, 1H), 6.12(s, 2H), 6.64(d, J=8.4 Hz, 2H), 7.01(d, J=8.4 Hz, 2H), 7.40(d, J=8.4 Hz, 2H), 7.90(d, J=8.4 Hz, 2H), 8.49(br, 3H), 8.70(br, 1H), 9.18(br, 1H), 9.54(br, 1H), 10.28(br, 1H), 12.95(br, 1H) MASS(m/e): 496(M$^+$+1)

EXAMPLE 14

Preparation of N'-[(S)-2-aminohexyl]-N-[(R)-3-methyl-1-[2-(4-carboxyphenyl)ethyl]butyl]-L-tyrosinamide dihydrochloride

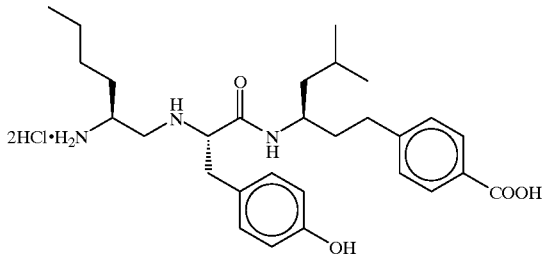

The title compound was obtained from N'-[(S)-2-aminohexyl]-N-[(S)-(E)-3-(4-carboxyphenyl)-1-(2-methylpropyl)-2-propenyl]-L-tyrosinamide according to the same hydrogenation as in Example 2.

$^1$H-NMR(DMSO-d$_6$, 400 Hz) δ (ppm) 0.81(d, J=6.4 Hz, 3H), 0.82(d, J=6.4 Hz, 3H), 0.86(t, J=6.7 Hz, 3H), 1.12–1.70 (m, 11H), 2.08–2.40(m, 2H), 2.68–3.60(m, 5H), 3.79(m, 1H), 4.03(m, 1H), 6.64(d, J=7.8 Hz, 2H), 7.05(d, J=7.8 Hz, 2H), 7.17(d, J=8.1 Hz, 2H), 7.83(d, J=8.1 Hz, 2H), 8.50(br, 3H), 9.31(br, 1H), 9.60(br, 1H), 10.25(br, 1H), 12.70(br, 1H) MASS(m/e): 497(M$^+$)

EXAMPLE 15

Preparation of N'-[(S)-2-aminohexyl]-N-[(S)-(E)-1-(2-methylpropyl)-3-(1-naphthyl)-2-propenyl]-L-tyrosinamide dihydrochloride

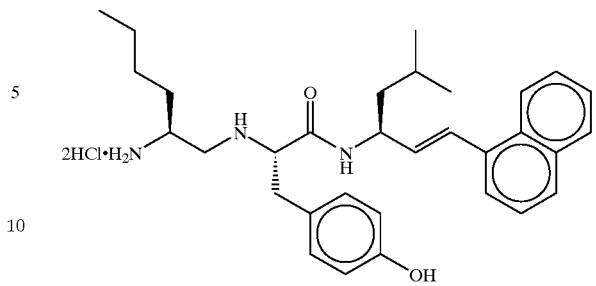

(1) Under an argon gas stream, N-[(S)-2-(tert-butoxycarbonylamino)hexyl]-L-tyrosine (384 mg, 0.80 mmol), 1-hydroxybenzotriazole monohydrate (135 mg, 0.88 mmol) and (S)-(E)-1-(1-naphthyl)-5-methyl-1-hexen-3-amine hydrocloride (1.8 g, 8.1 mmol) were suspended in tetrahydrofuran (5.0 ml), and cooled to –30° C. To the suspension was added a solution of triethylamine (161 mg, 1.6 mmol) and 1-ethyl-3-(3-dimethylaminopropyl) carbodiimide hydrochloride (169 mg, 0.88 mmol) in chloroform (5.0 ml), followed by stirring for 4 hours. After the reaction, 1 M hydrochloric acid was added to the mixture, followed by extraction with chloroform. The organic layer was washed with a saturated aqueous sodium bicarbonate solution, water and a saturated aqueous sodium chloride solution, successively, and dried over anhydrous sodium sulfate. The organic layer was concentrated under reduced pressure, and purified by column chromatography to give N'-(tert-butoxycarbonyl)-N'-[(S)-2-(tert-butoxycarbonylamino)hexyl]-N-[(S)-(E)-1-(2-methylpropyl)-3-(1-naphthyl)-2-propenyl]-L-tyrosinamide (540 mg).

(2) The title compound was obtained from N'-(tert-butoxycarbonyl)-N'-[(S)-2-(tert-butoxycarbonylamino)hexyl]-N-[(S)-(E)-1-(2-methylpropyl)-3-(1-naphthyl)-2-propenyl]-L-tyrosinamide dihydrochloride in the same manner as in Reference Example 2(3).

$^1$H-NMR(DMSO-d$_6$, 400 MHz) δ (ppm) 0.87(t, J=6.4 Hz, 3H), 0.92(d, J=7.0 Hz, 3H), 0.94(d, J=7.0 Hz, 3H), 1.15–1.73(m, 9H), 2.82–3.11(m, 2H), 3.11–3.30(m, 2H), 3.50(m, 1H), 4.06(m, 1H), 4.62(m, 1H), 5.94(dd, J=6.4, 15.6 Hz, 1H), 6.54(d, J=8.4 Hz, 2H), 7.02(d, J=8.4 Hz, 2H), 7.17(d, J=15.6 Hz, 1H), 7.48– 7.62(m, 4H), 7.83–8.00(m, 2H), 8.09(m, 1H), 8.58(br, 3H), 8.83(br, 1H), 9.25(s, 1H), 9.53(br, 1H), 10.31(br, 1H) MASS(m/e): 501(M$^+$)

EXAMPLE 16

Preparation of N'-[(S)-2-aminohexyl]-N-[(R)-3-methyl-1-[2-(1-naphthyl)ethyl]butyl]-L-tyrosinamide dihydrochloride

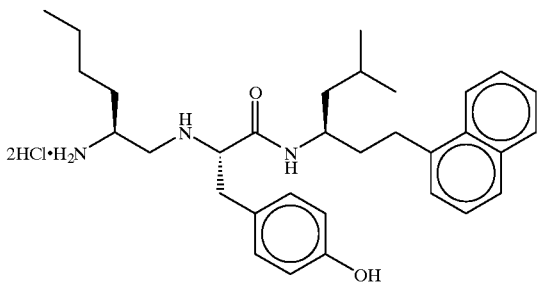

The title compound was obtained from N'-[(S)-2-aminohexyl]-N-[(S)-(E)-1-(2-methylpropyl)-3-(1-naphthyl)-2-propenyl]-L-tyrosinamide dihydrochloride according to the same hydrogenation as in Example 2.

$^1$H-NMR(DMSO-d$_6$, 400 MHz) δ (ppm) 0.83(d, J=6.6 Hz, 6H), 0.84(t, J=6.3 Hz, 3H), 1.12–1.74(m, 11H), 2.55–3.30(m, 6H), 3.47(m, 1H), 3.80–4.24(m, 2H), 6.63(d, J=8.3 Hz, 2H), 7.07(d, J=8.3 Hz, 2H), 7.21(m, 1H), 7.41(dd, J=7.1, 8.1 Hz, 1H), 7.46–7.58(m, 2H), 7.75(d, J=8.1 Hz, 1H), 7.90(m, 1H), 7.95(d, J=7.8 Hz, 1H), 8.56(br, 3H), 8.95–9.37(br, 2H), 9.58(br, 1H), 10.28(br, 1H) MASS(m/e): 503(M$^+$)

EXAMPLE 17

Preparation of N'-[(S)-2-aminohexyl]-N-[(S)-(E)-1-(2-methylpropyl)-3-phenyl-2-propenyl]-L-tyrosinamide dihydrochloride

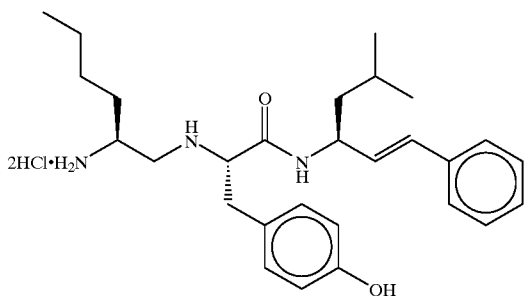

The title compound was obtained from N-(tert-butoxycarbonyl)-N-[(S)-2-(tert-butoxycarbonylamino)hexyl]-L-tyrosine and (S)-(E)-1-phenyl-5-methyl-1-hexen-3-amine hydrochloride in the same manner as in Example 1.

$^1$H-NMR(DMSO-d$_6$, 400 MHz) δ (ppm); 0.81–0.97(m, 9H), 1.18–1.50(m, 6H), 1.50–1.72(m, 3H), 2.88(m, 1H), 2.99(dd, J=10.0, 13.0 Hz, 1H), 3.10–3.30(m, 2H), 3.50(m, 1H), 4.05(m, 1H), 4.49(m, 1H), 5.96(dd, J=5.8, 16.1 Hz, 1H), 6.11(d, J=16.1 Hz, 1H), 6.63(d, J=8.4 Hz, 2H), 7.02(d, J=8.4 Hz, 2H), 7.18–7.41(m, 5H), 8.64(br, 3H), 8.75(d, J=7.0 Hz, 1H), 9.42(s, 1H), 9.57(br, 1H), 10.40(br, 1H) MASS(m/e): 451(M$^+$)

EXAMPLE 18

Preparation of N'-[(S)-2-aminohexyl]-N-[(R)-3-methyl-1-[2-phenylethyl]butyl]-L-tyrosinamide dihydrochloride

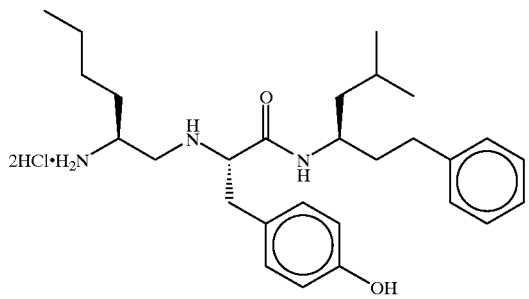

The title compound was obtained from N'-[(S)-2-aminohexyl]-N-[(S)-(E)-1-(2-methylpropyl)-3-phenyl-2-propenyl]-L-tyrosinamide dihydrochloride according to the same hydrogenation as in Example 2.

$^1$H-NMR(DMSO-d$_6$, 400 MHz) δ (ppm); 0.81(d, J=6.4 Hz, 3H), 0.83(d, J=6.5 Hz, 3H), 0.88(t, J=6.9 Hz, 3H), 1.12–1.70(m, 11H), 2.19(t, J=6.8 Hz, 2H), 2.82(m, 1H), 2.96(m, 1H), 3.07–3.32(m, 2H), 3.,48(m, 1H), 3.77(m, 1H), 4.04(m, 1H), 6.68(d, J=8.4 Hz, 2H), 7.00–7.06(m, 4H), 7.15(t, J=7.4 Hz, 1H), 7.25(t, J=7.4 Hz, 2H), 8.46(br, 1H), 8.56(br, 3H), 9.36(s, 1H), 9.58(br, 1H), 10.24(br, 1H) MASS (m/e): 453(M$^+$)

EXAMPLE 19

Preparation of N'-((S)-2-aminohexyl]-N-[(S)-(E)-3-(4-chlorophenyl)-1-(2-methylpropyl)-2-propenyl]-L-tyrosinamide dihydrochloride

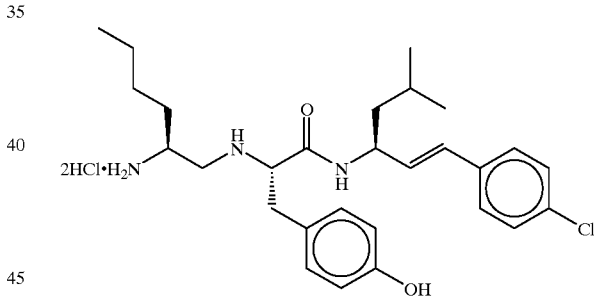

The title compound was obtained from N-(tert-butoxycarbonyl)-N-[(S)-2-(tert-butoxycarbonylamino)hexyl]-L-tyrosine and (S)-(E)-1-(4-chlorophenyl)-5-methyl-1-hexen-3-amine hydrochloride in the same manner as in Example 15.

$^1$H-NMR(DMSO-d$_6$, 400 MHz) δ (ppm); 0.80–0.95(m, 9H), 1.15–1.49(m, 6H), 1.49–1.72(m, 3H), 2.86(m, 1H), 2.97(dd, J=10.2, 12.9 Hz, 1H), 3.10–3.30(m, 2H), 3.49(m, 1H), 4.05(m, 1H), 4.49(m, 1H), 5.96(dd, J=5.3, 16.1 Hz, 1H), 6.05(d, J=16.1 Hz, 1H), 6.63(d, J=8.4 Hz, 2H), 7.01(d, J=8.4 Hz, 2H), 7.31(d, J=8.6 Hz, 2H), 7.38(d, J=8.6 Hz, 2H), 8.61(br, 3H), 8.73(d, J=7.3 Hz, 1H), 9.43(s, 1H), 9.58(br, 1H), 10.38(br, 1H) NASS(m/e): 485(M$^+$)

EXAMPLE 20

Preparation of N'-[(S)-2-aminohexyl]-N-[(S)-(Z)-3-(4-chlorophenyl)-1-(2-methylpropyl)-2-propenyl]-L-tyrosinamide dihydrochloride

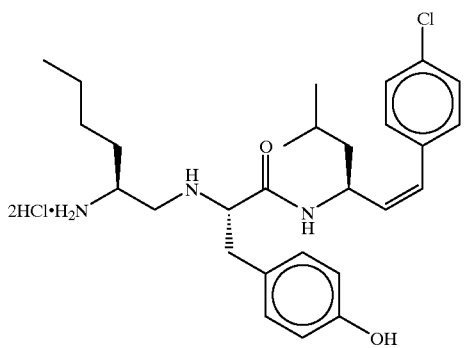

(1) Carrying out the same reaction as in Example 15(1) using N-(tert-butoxycarbonyl)-N-[(S)-2-(tert-butoxycarbonylamino)hexyl]-L-tyrosine and (S)-1-(4-chlorophenyl)-5-methyl-1-hexen-3-amine hydrochloride (a mixture of E:Z=1:1), followed by purification by column chromatography to give N'-(tert-butoxycarbonyl)-N'-[(S)-2-(tert-butoxycarbonylamino)hexyl]-N-[(S)-(Z)-3-(4-chlorophenyl)-1-(2-methylpropyl)-2-propenyl]-L-tyrosinamide.

(2) The title compound was obtained from N'-(tert-butoxycarbonyl)-N'-[(S)-2-(tert-butoxycarbonylamino) hexyl]-N-[(S)-(Z)-3-(4-chlorophenyl)-1-(2-methylpropyl)-2-propenyl]-L-tyrosinamide in the same manner as in Reference Example 2(3).

$^1$H-NMR(DMSO-$d_6$, 400 MHz) δ (ppm); 0.65(d, J=6.3 Hz, 3H), 0.78(d, J=6.3 Hz, 3H), 0.87(t, J=6.7 Hz, 3H), 1.13–1.35(m, 5H), 1.36–1.50(m, 2H), 1.50–1.70(m, 2H), 2.86(m, 1H), 3.02(m, 1H), 3.09–3.26(m, 2H), 3.48(m, 1H), 3.98(m, 1H), 4.79(m, 1H), 5.29(dd, J=10.1, 10.1 Hz, 1H), 6.43(d, J=10.1 Hz, 1H), 6.64(d, J=8.5 Hz, 2H), 7.00(d, J=8.5 Hz, 2H), 7.38(d, J=8.8 Hz, 2H), 7.41(d, J=8.8 Hz, 2H), 8.51(br, 3H), 8.76(br, 1H), 9.36(br, 1H), 9.42(br, 1H), 10.20 (br, 1H) MASS(m/e): 485(M$^+$)

EXAMPLE 21

Preparation of N'-[(S)-2-aminohexyl]-N-[(S)-(E)-3-([1,1'-biphenyl]-4-yl)-1-(2-methylpropyl)-2-propenyl]-L-tyrosinamide dihydrochloride

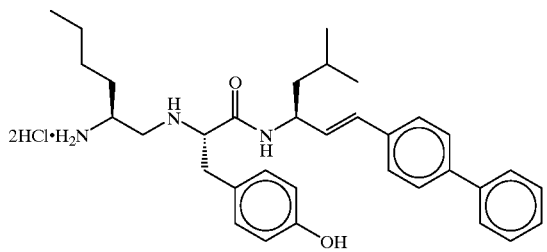

The title compound was obtained from N-(tert-butoxycarbonyl)-N-[(S)-2-(tert-butoxycarbonylamino) hexyl]-L-tyrosine and (S)-(E)-1-([1,1'-biphenyl]-4-yl)-5-methyl-1-hexen-3-amine hydrochloride in the same manners as in Examples 15(1) and (2)

$^1$H-NMR(DMSO-$d_6$, 400 MHz) δ (ppm); 0.88(t, J=7.0 Hz, 3H), 0.89(d, J=6.1 Hz, 3H), 0.90(d, J=6.8 Hz, 3H), 1.13–1.72(m, 9H), 2.71–3.70(m, 5H), 4.04(m, 1H), 4.52(m, 1H), 6.02(dd, J=5.1, 16.1 Hz, 1H), 6.16(d, J=16.1 Hz, 1H), 6.67(d, J=8.4 Hz, 2H), 7.03(d, J=8.4 Hz, 2H), 7.32–7.74(m, 9H), 8.54(br, 3H), 8.72(br, 1H), 9.42(s, 1H), 9.54(br, 1H), 10.30(br, 1H) MASS(m/e): 527(M$^+$)

EXAMPLE 22

Preparation of N'-[(S)-2-aminohexyl]-N-[(R)-1-[2-([1,1'-biphenyl]-4-yl)ethyl]-3-methylbutyl]-L-tyrosinamide dihydrochloride

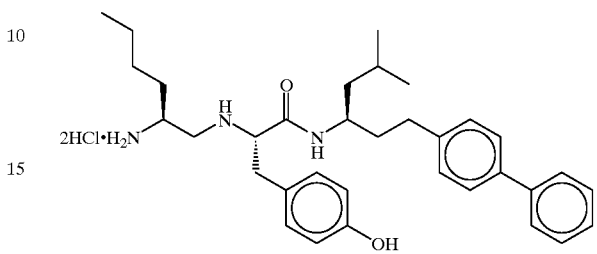

The title compound was obtained from N'-[(S)-2-aminohexyl]-N-[(S)-(E)-3-([1,1'-biphenyl]-4-yl)-1-(2-methylpropyl)-2-propenyl]-L-tyrosinamide dihydrochloride according to the same hydrogenation as in Example 2.

$^1$H-NMR(DMSO-$d_6$, 400 MHz) δ (ppm); 0.75–0.95(m, 9H), 1.10–1.66(m, 11H), 2.22–2.58(m, 3H), 2.58–2.86(m, 3H), 3.02(m, 1H), 3.25(m, 1H), 3.83(m, 1H), 6.43(br, 3H), 6.66(d, J=8.3 Hz, 2H), 7.03(d, J=8.3 Hz, 2H), 7.18(d, J=8.2 Hz, 2H), 7.34(m, 1H), 7.41–7.51(m, 2H), 7.55(d, J=8.2 Hz, 2H), 7.59–7.68(m, 2H), 7.75(m, 1H), 9.20(s, 1H) MASS(m/e): 530(M$^+$+1)

EXAMPLE 23

Preparation of N'-[(S)-2-aminohexyl]-N-[(S)-(E)-3-(2-quinolyl)-1-(2-methylpropyl)-2-propenyl]-L-tyrosinamide trihydrochloride

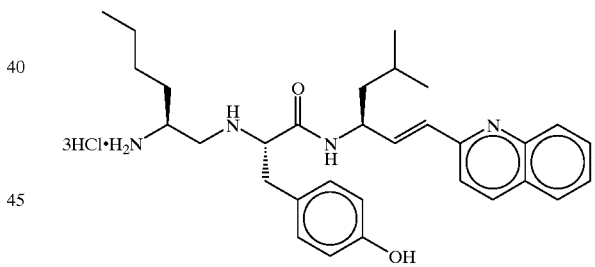

The title compound was obtained from N-(tert-butoxycarbonyl)-N-[(S)-2-(tert-butoxycarbonylamino) hexyl]-L-tyrosine and (S)-(E)-1-(2-quinolyl)-5-methyl-1-hexen-3-amine dihydrochloride in the same manner as in Example 15.

$^1$H-NMR(DMSO-$d_6$, 400 MHz) δ (ppm); 0.87(t, J=6.8 Hz, 3H), 0.90(d, J=7.0 Hz, 3H). 0.92(d, J=6.9 Hz, 3H), 1.19–1.38(m, 4H), 1.41–1.68(m, 5H), 2.93(m, 1H), 3.20(dd, J=9.1, 13.4 Hz, 1H), 3.13–3.34(m, 3H), 4.13(m, 1H), 4.62 (m, 1H), 6.60(d, J=8.5 Hz, 2H), 6.74(d, J=17.0 Hz, 1H), 6.88(m, 1H), 7.05(d, J=8.5 Hz, 2H), 7.78(t, J=7.3 Hz, 1H), 7.86–8.06(m, 2H), 8.19(d, J=8.1 Hz, 1H), 8.33(m, 1H), 8.59(br, 3H), 8.82(br, 1H), 9.01(d, J=8.0 Hz, 1H), 9.27(br, 1H), 9.58(br, 1H), 10.28(br, 1H) MASS(m/e): 503(M$^+$+1)

EXAMPLE 24

Preparation of N'-[(S)-2-aminohexyl]-N-[(R)-3-methyl-1-[2-(2-quinolyl)ethyl]butyl]-L-tyrosinamide dihydrochloride

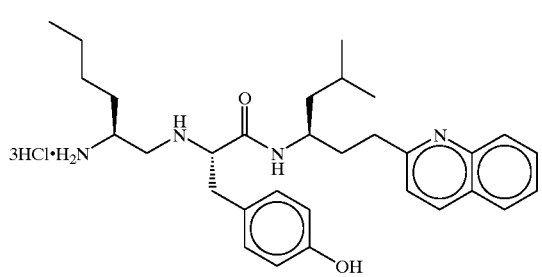

The title compound was obtained from N'-[(S)-2-aminohexyl]-N-[(S)-(E)-3-(2-quinolyl)-1-(2-methylpropyl)-2-propenyl]-L-tyrosinamide trihydrochloride according to the same hydrogenation as in Example 2.

¹H-NMR(DMSO-$d_6$, 400 MHz) δ (ppm); 0.83(d, J=6.7 Hz, 3H), 0.85(d, J=6.5 Hz, 3H), 0.87(t, J=6.8 Hz, 3H), 1.16–1.44(m, 6H), 1.46–1.72(m, 4H), 1.79(m, 1H), 2.54(m, 1H), 2.76(m, 1H), 2.87(m, 1H), 2.96(dd, J=10.5, 13.1 Hz, 1H), 3.18–3.22(m, 2H), 3.65(m, 1H), 3.82(m, 1H), 4.16(m, 1H), 6.62(d, J=8.5 Hz, 2H), 7.09(d, J=8.5 Hz, 2H), 7.67(m, 1H), 7.87(m, 1H), 8.07(m, 1H), 8.28(m, 1H), 8.40(m, 1H), 8.65(br, 3H), 8.28(d, J=7.8 Hz, 1H), 8.97(br, 1H), 9.17(br, 1H), 9.69(br, 1H), 10.38(br, 1H) MASS(m/e): 504(M⁺)

EXAMPLE 25

Preparation of N'-[(S)-2-aminohexyl]-N-[(S)-1-(2-methylpropyl)-2-propenyl]-L-tyrosinamide dihydrochloride

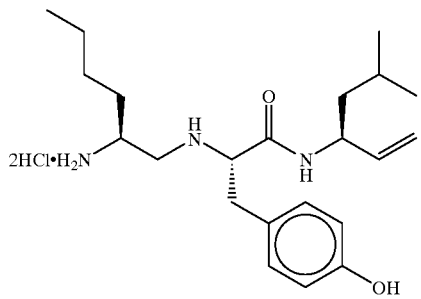

The title compound was obtained from N-(tert-butoxycarbonyl)-N-[(S)-2-(tert-butoxycarbonylamino)hexyl]-L-tyrosine and (S)-5-methyl-1-hexen-3-amine hydrochloride in the same manner as in Example 15.

¹H-NMR(DMSO-$d_6$, 400 MHz) δ (ppm); 0.84(d, J=7.0 Hz, 3H), 0.85(d, J=6.9 Hz, 3H), 0.86(t, J=6.0 Hz, 3H), 1.15–1.40(m, 6H), 1.44–1.70(m, 3H), 2.83(m, 1H), 2.94(dd, J=9.8, 12.8 Hz, 1H), 3.08–3.24(m, 2H), 3.48(m, 1H), 4.00 (m, 1H), 4.32(m, 1H), 4.59(d, J=17.3 Hz, 1H), 4.84(dt, J=10.5 Hz, 1H), 5.54(ddd, J=5.4, 10.5, 17.3 Hz, 1H), 6.68(d, J=8.5 Hz, 2H), 6.99(d, J=8.5 Hz, 2H), 8.37–8.73(br, 4H), 9.39(br, 1H), 9.55(br, 1H), 10.33(br, 1H) MASS(m/e): 376 (M⁺+1)

EXAMPLE 26

Preparation of N'-[(S)-2-aminohexyl]-N-[(R)-1-ethyl-3-methylbutyl]-L-tyrosinamide dihydrochloride

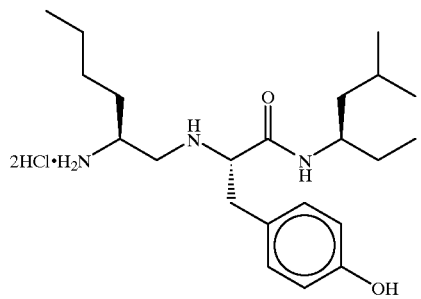

The title compound was obtained from N'-[(S)-2-aminohexyl]-N-[(S)-1-(2-methylpropyl)-2-propenyl]-L-tyrosinamide dihydrochloride according to the same hydrogenation as in Example 2.

¹H-NMR(DMSO-$d_6$, 400 MHz) δ (ppm); 0.48(t, J=7.4 Hz, 3H), 0.81(d, J=6.6 Hz, 3H), 0.83(d, J=6.7 Hz, 3H), 0.87(t, J=6.9 Hz, 3H), 1.02–1.38(m, 8H), 1.41–1.72(m, 3H), 2.81(m, 1H), 2.91(dd, J=9.9, 12.8 Hz, 1H), 3.08–3.25(m, 2H), 3.48(m, 1H), 3.67(m, 1H), 3.97(m, 1H), 6.80(d, J=8.5 Hz, 2H), 7.00(d, J=8.5 Hz, 2H), 8.31(d, J=8.4 Hz, 1H), 8.61(br, 3H), 9.38(br, 1H), 9.56(br, 1H), 10.34(br, 1H) MASS(m/e): 377(M⁺)

EXAMPLE 27

Preparation of N-[(S)-1-[(4-hydroxyphenyl)methyl]-2-[(S)-(E)-[1-(2-methylpropyl)-3-phenyl-2-propenyl]amino]ethyl]-L-norleucinamide dihydrochloride

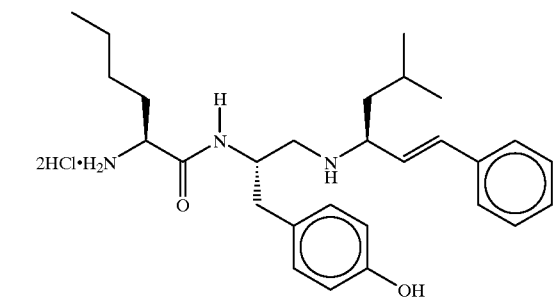

The title compound was obtained from N-(tert-butoxycarbonyl)-N-[(S)-2-(tert-butoxycarbonylamino)hexyl]-L-tyrosine and (S)-(E)- 1-phenyl-5-methyl-1-hexen-3-amine hydrochloride in the same manner as in Example 15.

¹H-NMR(DMSO-$d_6$, 400 MHz) δ (ppm); 0.80(t, J=6.9 Hz, 3H), 0.88(d, J=6.5 Hz, 3H), 0.91(d, J=6.6 Hz, 3H), 1.04–1.27(m, 4H), 1.46–1.85(m, 5H), 2.76–2.87(m, 2H), 2.97(m, 1H), 3.16(m, 1H), 3.59(m, 1H), 3.84(m, 1H), 4.04 (m, 1H), 6.15(dd, J=9.5, 15.8 Hz, 1H), 6.64(d, J=8.5 Hz, 2H), 6.83(d, J=15.8 Hz, 1H), 7.00(d, J=8.5 Hz, 2H), 7.30–7.51(m, 5H), 8.27(br, 3H), 8.67(d, J=6.9 Hz, 1H), 9.00–9.30(m, 2H), 9.25(s, 1H) MASS(m/e): 451(M⁺)

EXAMPLE 28

Preparation of N-[1-[(S)-[(4-hydroxyphenyl)methyl]]-2-[[(R)-3-methyl-1-(2-phenylethyl)butyl]amino]ethyl]-L-norleucinamide dihydrochloride

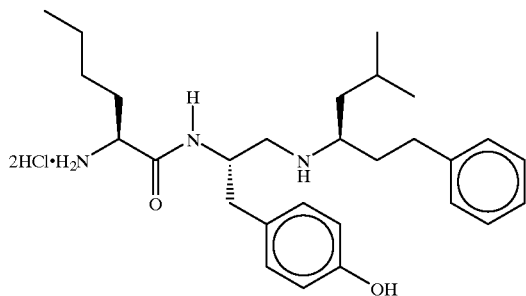

The title compound was obtained from N-[(S)-1-[(4-hydroxyphenyl)methyl]-2-[(S)-(E)-[1-(2-methylpropyl)-3-phenyl-2-propenyl]amino]ethyl]-L-norleucinamide dihydrochloride according to the same hydrogenation as in Example 2.

$^1$H-NMR(DMSO-d$_6$, 400 MHz) δ (ppm); 0.82(t, J=6.8 Hz, 3H), 0.83(d, J=6.2 Hz, 3H), 0.88(d, J=6.5 Hz, 3H), 1.08–1.32(m, 4H), 1.42–1.59(m, 2H), 1.59–1.79(m, 3H), 1.81–2.02(m, 2H), 2.62–2.75(m, 2H), 2.80(dd, J=6.3, 14.0 Hz, 1H), 2.86(dd, J=8.1, 14.0 Hz, 1H), 3.02(m, 1H), 3.15(m, 1H), 3.25(m, 1H), 3.62(t, J=6.4 Hz, 1H), 4.06(m, 1H), 6.70(d, J=8.4 Hz, 2H), 7.04(d, J=8.4 Hz, 2H), 7.14–7.34(m, 5H), 8.04–8.60(br, 3H), 8.60–9.40(br, 2H), 8.83(d, J=7.5 Hz, 1H), 9.32(s, 1H)

EXAMPLE 29

Preparation of (S)-(E)-N-[(S)-2-[[(S)-2-aminohexyl]amino]-3-(4-hydroxyphenyl)propyl]-5-methyl-1-phenyl-1-hexen-3-amine trihydrochloride

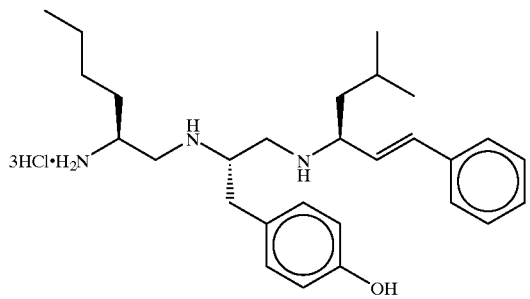

The title compound was obtained from N-[(S)-2-(tert-butoxycarbonylamino)hexyl]-L-tyrosine methyl ester and (S)-(E)-5-methyl-1-phenyl-1-hexen-3-amine hydrochloride in the same manners as in Reference Examples 1(1) and 2(3).

$^1$H-NMR(DMSO-d$_6$, 400 MHz) δ (ppm); 0.81–0.96(m, 9H), 1.21–1.41(m, 4H), 1.47–1.80(m, 5H), 2.80–3.70(m, 7H), 3.72–4.00(m, 2H), 6.04(dd, J=9.7, 15.6 Hz, 1H), 6.59(d, J=8.3 Hz, 2H), 6.81(d, J=15.6 Hz, 1H), 7.03–7.22(m, 2H), 7.30–7.46(m, 5H), 8.58(br, 3H), 9.40(br, 1H), 9.70(br, 2H), 9.95(br, 1H), 10.34(br, 1H) MASS(m/e): 438(M$^+$+1)

EXAMPLE 30

Preparation of (R)-N-[(S)-2-[[(S)-2-aminohexyl]amino]-3-(4-hydroxyphenyl)propyl]-5-methyl-1-phenylhexan-3-amine trihydrochloride

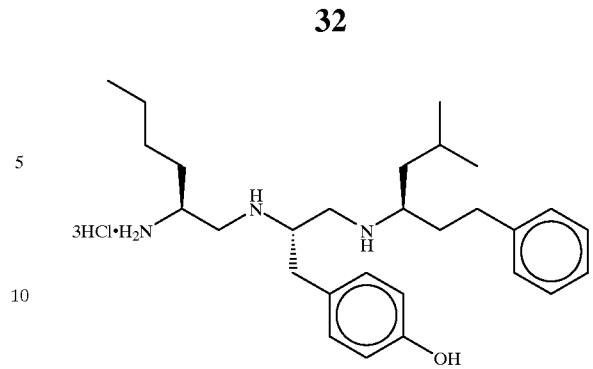

The title compound was obtained from (S)-(E)-N-[(S)-2-[[(S)-2-aminohexyl]amino]-3-(4-hydroxyphenyl)propyl]-5-methyl-1-phenyl-1-hexen-3-amine trihydrochloride according to the same hydrogenation as in Example 2.

$^1$H-NMR(DMSO-d$_6$, 400 MHz) δ (ppm); 0.76(d, J=6.2 Hz, 3H), 0.84(d, J=6.4 Hz, 3H), 0.89(t, J=7.0 Hz, 3H), 1.02–1.95(m, 11H), 2.36–2.69(m, 4H), 2.74–3.34(m, 5H), 3.63(m, 1H), 3.93(m, 1H), 6.75(d, J=8.1 Hz, 2H), 7.08–7.34 (m, 7H), 8.53(br, 3H), 9.08–9.75(m, 3H), 10.16–10.64(m, 2H) MASS(m/e): 440(M$^+$+1)

EXAMPLE 31

Preparation of N-[(S)-2-[[(S)-2-aminohexyl]amino]-3-(4-hydroxyphenyl)propyl]-L-isoleucine methyl ester trihydrochloride

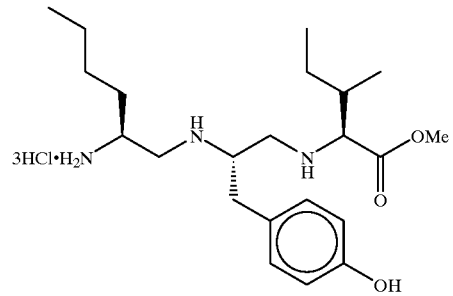

The title compound was obtained from N-[(tert-butoxycarbonyl)-L-norleucyl]-L-tyrosine methyl ester and L-isoleucine methyl ester hydrochloride in the same manners as in Reference Examples 1(1) and 2(3).

$^1$H-NMR(DMSO-d$_6$, 400 MHz) δ (ppm); 0.86(d, J=6.6 Hz, 3H), 0.87(t, J=6.8 Hz, 3H), 0.89(t, J=7.1 Hz, 3H), 1.18–1.52(m, 6H), 1.59–1.78(m, 2H), 2.04(m, 1H), 2.79(m, 1H), 3.06(m, 1H), 3.21(m, 1H), 3.33(m, 1H), 3.44–4.40(m, 5H), 3.66(s, 3H), 6.76(d, J=8.2 Hz, 2H), 7.15(d, J=8.2 Hz, 2H), 8.64(br, 3H), 9.20–10.80(br, 5H) MASS(m/e): 394 (M$^+$+1)

Test Example

The binding capability to angiotensin IV receptor was measured by using Hartley guinea pig hippocampus referring to the method described by Miller-Wing et al., J. Pharmacol. Exp. Ther., vol. 266, pp.1718 (1993).

The Hartley guinea pig hippocampus was homogenized in a 50 mM Tris hydrochloride buffer solution (pH 7.4) containing 1 mM ethylenediamine-N,N,N',N'-tetraacetic acid (EDTA) and 100 μM phenylmethanesulfonyl fluoride (PMSF). After centrifugation at 900× g, the resulting supernatant was further centrifuged at 48,000× g. The precipitate was washed once with the same buffer solution and suspended in 50 mM Tris hydrochloride buffer solution (pH 7.4) containing 150 mM sodium chloride, 1 mM EDTA, 100 μM PMSF and 0.1% bovine serum albumin (BSA) to give a protein concentration of 50 μkg/ml as a crude membrane specimen.

The resulting membrane specimen was reacted with 0.2 nM $^{125}$I-angiotensin IV and a test compound dissolved in dimethyl sulfoxide at 37° C. for 90 minutes. $^{125}$I-angiotensin IV binding to the membrane was filtered under suction on GF/B filter paper with the use of a cell harvester for laboratory. The radioactivity on the filter paper was measured by using a gamma-counter. The non-specific bond was measured in the presence of 1 μM angiotensin IV, and the specific bond was calculated by subtracting the non-specific bond from the total bond. The binding capability ($IC_{50}$) of the test compound to angiotensin IV receptor was measured as the concentration of the test compound for 50% inhibition of binding from the inhibition curve obtained by reacting 0.2 nM $^{125}$I-angiotensin IV with the test compound at various concentrations. Results are shown in Table 1.

TABLE 1

| Test compound (Example No.) | $IC_{50}$ (nM) | Test compound (Example No.) | $IC_{50}$ (nM) |
| --- | --- | --- | --- |
| 1 | 0.59 | 17 | 0.65 |
| 2 | 4.13 | 18 | 8.70 |
| 3 | 12.62 | 19 | 0.53 |
| 4 | 11.50 | 20 | 5.46 |
| 5 | 7.22 | 21 | 6.00 |
| 6 | 18.31 | 22 | 89.02 |
| 7 | 0.93 | 23 | 0.53 |
| 8 | 15.20 | 24 | 3.77 |
| 9 | 22.05 | 25 | 89.02 |
| 10 | 81.11 | 26 | 38.54 |
| 11 | 1.23 | 27 | 327.5 |
| 12 | 35.11 | 28 | 298.6 |
| 13 | 1.79 | 29 | 24.20 |
| 14 | 26.56 | 30 | 170.7 |
| 15 | 3.76 | 31 | 31.99 |
| 16 | 3.43 | | |

Industrial Applicability

The novel amino compounds of the present invention are useful as medicines, in particular, as therapeutical drugs (antagonist or agonist) for various diseases in which angiotensin IV participates, for example, acceleration of renal blood flow, cerebral vasodilation, inhibition of cell proliferation and hypermnesia, since they act on angiotensin IV receptor agonistically.

For these purposes, the compounds of the present invention can be prepared in the forms, such as tablets, pills, capsules, granules, powders, solutions, emulsions, suspensions and injections using ordinary fillers, binders, disintegrators, pH regulators and solubilizers according to ordinary preparation techniques.

The compounds of the present invention can be administered orally or parenterally to an adult patient in an amount of 0.01 to 300 mg/day in a single dose or several divided doses. This dose can be increased or decreased depending on the kind of diesease, the age, body weight and conditions of the patient.

What is claimed is:

1. An amino compound represented by Formula (1):

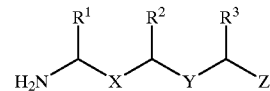

wherein X is $CH_2NH$ or CONH, Y is $CH_2NH$ or CONH with the proviso that X and Y are not CONH at the same time; Z is $CH=C(R^4)R^5$, $CH_2CH(R^4)R^5$ or an alkoxycarbonyl group, $R^1$ is a hydrogen atom; a lower alkyl group, a cycloalkyl group, a cycloalkyl-substituted alkyl group, an aralkyl group or an aryl group, each group of which is substituted or unsubstituted, $R^2$ and $R^3$ are each independently a lower alkyl group or an aralkyl group, each group of which is substituted or unsubstituted, and $R^4$ and $R^5$ are each independently a hydrogen atom; an alkyl group, an aralkyl group, an aryl group or a heteroaryl group, each group of which is substituted or unsubstituted, or a pharmaceutically acceptable salt thereof.

2. The amino compound or the pharmaceutically acceptable salt thereof according to claim 1, wherein X is $CH_2NH$.

3. The amino compound or the pharmaceutically acceptable salt thereof according to claim 1, wherein $R^2$ is a 4-hydroxybenzyl group.

4. The amino compound or the pharmaceutically acceptable salt thereof according to claim 2, wherein Y is CONH.

5. The amino compound or the pharmaceutically acceptable salt thereof according to claim 3, wherein X is $CH_2NH$, $R^1$ is a lower alkyl group or an aralkyl group, each of which is substituted or unsubstituted, $R^3$ is a substituted or unsubstituted lower alkyl group, and Z is $CH=C(R^4)R^5$ or $CH_2CH(R^4)R^5$.

6. The amino compound or the pharmaceutically acceptable salt thereof according to claim 5, wherein Z is $CH=C(R^4)R^5$.

7. The amino compound or the pharmaceutically acceptable salt thereof according to claim 6, wherein $R^1$ is a group selected from the group consisting of a propyl group, an isopropyl group, a butyl group, an isobutyl group, a sec-butyl group and a 2-methylthioethyl group.

8. A medicine comprising the amino compound or the pharmaceutically acceptable salt thereof according to any one of claims 1 to 7.

9. An angiotensin IV receptor agonist comprising the amino compound or the pharmaceutically acceptable salt thereof according to any one of claims 1 to 7 as an effective component.

10. A method for preventing or treating diseases in which angiotensin IV participates, which method comprises administering an effective amount of the amino compound or the pharmaceutically acceptable salt thereof according to any one of claims 1 to 7 to a patient in need thereof.

11. The method according to claim 10, wherein the diseases are acceleration of renal blood flow, cerebral vasodilation, inhibition of cell proliferation and hypermnesia.

12. The amino compound or the pharmaceutically acceptable salt thereof according to claim 1, wherein $R^1$ is a lower alkyl group, a cycloalkyl group, a cycloalkyl-substituted alkyl group, an aralkyl group or an aryl group, each group of which is substituted or unsubstituted.

* * * * *